(12) United States Patent
Vaska et al.

(10) Patent No.: US 9,610,190 B2
(45) Date of Patent: Apr. 4, 2017

(54) METHODS AND SYSTEMS FOR IMPROVING AIRWAY PATENCY

(71) Applicant: Apnicure, Inc., Redwood City, CA (US)

(72) Inventors: Matthias Vaska, Palo Alto, CA (US); Jonathan Podmore, San Carlos, CA (US); John Edwards Crowe, Menlo Park, CA (US); Sean Christopher Daniel, Palo Alto, CA (US)

(73) Assignee: Apnicure, Inc., Redwood City, CA (US)

( * ) Notice: Subject to any disclaimer, the term of this patent is extended or adjusted under 35 U.S.C. 154(b) by 0 days.

(21) Appl. No.: 14/626,097

(22) Filed: Feb. 19, 2015

(65) Prior Publication Data

US 2015/0157492 A1    Jun. 11, 2015

Related U.S. Application Data

(63) Continuation of application No. 13/912,021, filed on Jun. 6, 2013, now abandoned, which is a continuation
(Continued)

(51) Int. Cl.
*A61F 5/56*    (2006.01)
*A61M 16/04*    (2006.01)

(52) U.S. Cl.
CPC ......... *A61F 5/566* (2013.01); *A61M 16/0463* (2013.01); *A61M 16/0488* (2013.01);
(Continued)

(58) Field of Classification Search
CPC combination set(s) only.
See application file for complete search history.

(56) References Cited

U.S. PATENT DOCUMENTS

| 3,132,647 A | 5/1964 | Corniello |
| 4,169,473 A | 10/1979 | Samelson |

(Continued)

FOREIGN PATENT DOCUMENTS

| EP | 1862152 A1 | 12/2007 |
| JP | 2004522483 | 7/2004 |

(Continued)

OTHER PUBLICATIONS

Notice of allowance dated Feb. 5, 2014 for U.S. Appl. No. 13/368,182.
(Continued)

*Primary Examiner* — Ophelia A Hawthorne
(74) *Attorney, Agent, or Firm* — Wilson, Sonsini, Goodrich & Rosati

(57) ABSTRACT

An oral device for improving airway patency includes a tongue constraint and a negative pressure source. The tongue constraint engages the patient's tongue to maintain a clear region below the palate in an oral cavity and allow an anterior portion of the tongue to rise. By applying a negative pressure in the clear region, an airway behind the soft palate or tongue of the patient can be maintained. The tongue constraint is usually connected to an anchor. The anchor may be held between the patient's teeth or may engage the inferior surface of the palate. Another oral device for improving airway patency includes a lateral tongue structure and a negative pressure source.

16 Claims, 36 Drawing Sheets

Related U.S. Application Data of application No. 12/882,054, filed on Sep. 14, 2010, now Pat. No. 8,505,540, which is a continuation-in-part of application No. 12/269,683, filed on Nov. 12, 2008, now Pat. No. 8,122,889, and a continuation-in-part of application No. 12/840,076, filed on Jul. 20, 2010, now Pat. No. 8,573,223.

(60) Provisional application No. 60/987,707, filed on Nov. 13, 2007.

(52) U.S. Cl.
CPC ............. *A61M 2210/0637* (2013.01); *A61M 2210/0643* (2013.01)

(56) References Cited

U.S. PATENT DOCUMENTS

| | | | |
|---|---|---|---|
| 4,304,227 A | 12/1981 | Samelson | |
| 4,669,459 A | 6/1987 | Spiewak et al. | |
| 4,676,240 A | 6/1987 | Gardy | |
| 5,050,616 A | 9/1991 | Wolff et al. | |
| 5,104,315 A | 4/1992 | McKinley | |
| 5,465,734 A | 11/1995 | Alvarez et al. | |
| 5,513,986 A | 5/1996 | Feltham et al. | |
| 5,588,836 A | 12/1996 | Landis et al. | |
| 5,915,385 A | 6/1999 | Hakimi | |
| 5,957,133 A * | 9/1999 | Hart | A61F 5/566 128/200.26 |
| 5,989,193 A | 11/1999 | Sullivan | |
| 6,454,724 B1 | 9/2002 | Greene | |
| 6,467,484 B1 | 10/2002 | De Voss | |
| 6,494,209 B2 | 12/2002 | Kulick | |
| 6,675,802 B1 | 1/2004 | Thornton | |
| 6,679,257 B1 | 1/2004 | Robertson et al. | |
| 6,820,617 B2 | 11/2004 | Robertson et al. | |
| 6,877,513 B2 | 4/2005 | Scarberry et al. | |
| 6,955,172 B2 | 10/2005 | Nelson et al. | |
| 6,976,491 B2 | 12/2005 | D'Agosto | |
| 6,997,186 B2 | 2/2006 | Robertson et al. | |
| 7,073,505 B2 | 7/2006 | Nelson et al. | |
| 7,073,506 B2 | 7/2006 | Robertson et al. | |
| 7,182,082 B2 | 2/2007 | Hoffrichter | |
| 7,328,698 B2 | 2/2008 | Scarberry et al. | |
| 7,451,766 B2 | 11/2008 | Miller | |
| 7,509,164 B2 | 3/2009 | Jensen et al. | |
| 7,935,065 B2 | 5/2011 | Martin et al. | |
| 8,074,656 B2 | 12/2011 | Vaska et al. | |
| 8,091,554 B2 | 1/2012 | Jiang | |
| 8,122,889 B2 * | 2/2012 | Vaska | A61F 5/566 128/200.24 |
| 8,122,890 B2 | 2/2012 | Vaska et al. | |
| 8,505,540 B2 | 8/2013 | Vaska et al. | |
| 8,656,922 B2 | 2/2014 | Vaska et al. | |
| 8,701,672 B2 | 4/2014 | Vaska | |
| 9,549,795 B2 | 1/2017 | Podmore et al. | |
| 2001/0047805 A1 | 12/2001 | Scarberry et al. | |
| 2005/0081859 A1 | 4/2005 | Scarberry et al. | |
| 2005/0166928 A1 | 8/2005 | Jiang | |
| 2005/0166929 A1 | 8/2005 | Jiang | |
| 2005/0236003 A1 | 10/2005 | Meader | |
| 2006/0096600 A1 | 5/2006 | Witt et al. | |
| 2006/0282010 A1 | 12/2006 | Martin et al. | |
| 2007/0277818 A1 * | 12/2007 | Chen | A61F 5/566 128/200.24 |
| 2008/0188947 A1 | 8/2008 | Sanders | |
| 2008/0210244 A1 | 9/2008 | Keropian | |
| 2008/0216843 A1 | 9/2008 | Jiang | |
| 2008/0308112 A1 | 12/2008 | Aarts | |
| 2009/0120446 A1 | 5/2009 | Vaska et al. | |
| 2009/0120447 A1 | 5/2009 | Vaska et al. | |
| 2009/0123886 A1 | 5/2009 | Vaska et al. | |
| 2010/0147302 A1 | 6/2010 | Selvarajan et al. | |
| 2011/0220124 A1 | 9/2011 | Vaska et al. | |
| 2012/0017917 A1 | 1/2012 | Podmore et al. | |
| 2012/0132215 A1 | 5/2012 | Vaska et al. | |
| 2012/0132216 A1 | 5/2012 | Vaska | |
| 2013/0263866 A1 | 10/2013 | Vaska et al. | |

FOREIGN PATENT DOCUMENTS

| | | |
|---|---|---|
| WO | WO 2004/021869 A2 | 3/2004 |
| WO | WO 2005/074480 A2 | 8/2005 |
| WO | WO-2005082452 A1 | 9/2005 |
| WO | WO 2005/092331 A1 | 10/2005 |

OTHER PUBLICATIONS

Office action dated Jun. 20, 2014 for U.S. Appl. No. 13/912,021.
Office action dated Nov. 21, 2014 for U.S. Appl. No. 13/912,021.
Cartwright et al., "The effects of a non-surgical treatment for obstructive sleep apnea: the tongue retaining device;" JAMA, Aug. 1982; 248(6): 705-709.
Engelke et al., "Preliminary radiographic observations of the tongue-repositioning manoeuvre" Eur. J. of Orthodontics, 2006; 28: 618-623.
European search report dated Oct. 23, 2012 for EP Application No. 08849727.6.
Hoffstein. Review of oral appliances for treatment of sleep-disordered breathing. Sleep Breath, 2007 Mani 1(1):1-22.
International Search Report and Written Opinion dated Mar. 17, 2009 for PCT Application No. US2008/083440.
Office action dated Jan. 15, 2013 for U.S. Appl. No. 12/882,054.
Office action dated Mar. 17, 2011 for U.S. Appl. No. 12/269,708.
Office action dated May 25, 2011 for U.S. Appl. No. 12/269,700.
Office action dated Jun. 4, 2013 for U.S. Appl. No. 13/365,791.
Office action dated Jul. 26, 2011 for U.S. Appl. No. 12/269,708.
Office action dated Aug. 19, 2011 for U.S. Appl. No. 12/269,683.
Office action dated Oct. 15, 2012 for U.S. Appl. No. 12/882,054.
Notice of allowance dated May 8, 2013 for U.S. Appl. No. 12/882,054.
Notice of allowance dated Sep. 19, 2011 for U.S. Appl. No. 12/269,700.
Notice of allowance dated Oct. 27, 2012 for U.S. Appl. No. 12/269,708.
Notice of allowance dated Nov. 15, 2011 for U.S. Appl. No. 12/269,683.
Notice of allowance dated Nov. 27, 2013 for U.S. Appl. No. 13/365,791.
European search report and search opinion dated Sep. 8, 2015 for EP Application No. 15168256-4.
Co-pending U.S. Appl. No. 15/376,368, filed Dec. 12, 2016.

* cited by examiner

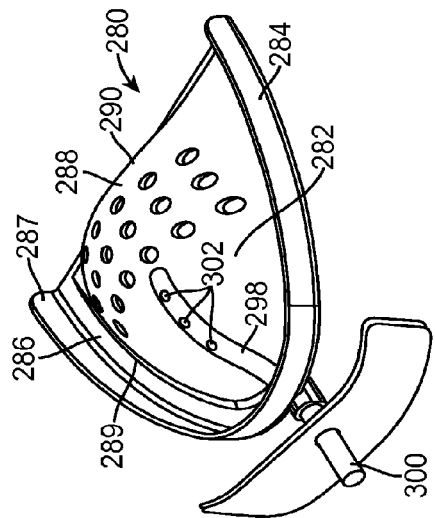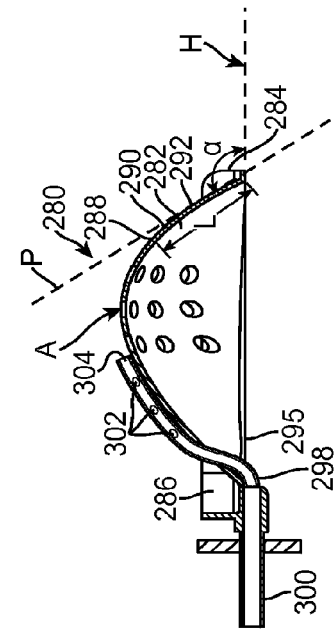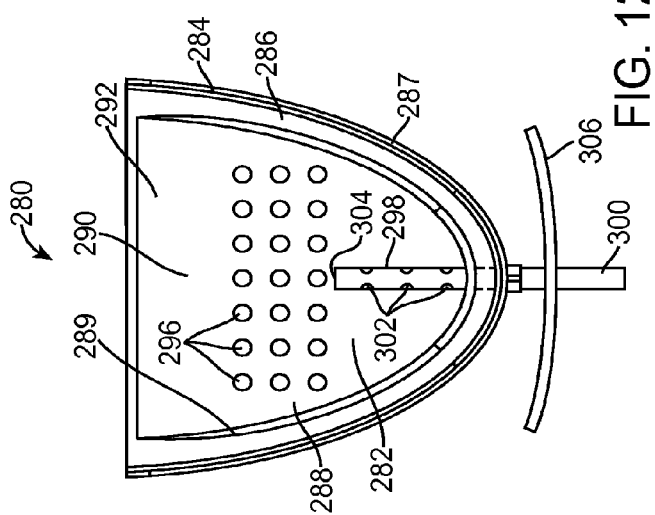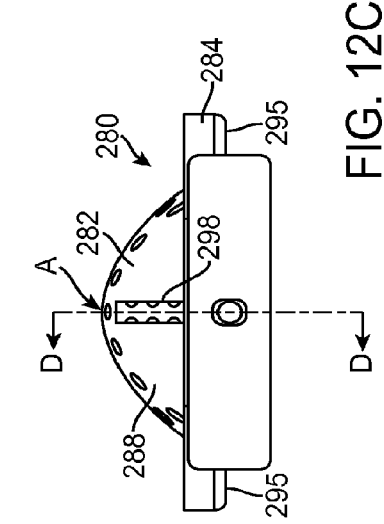
FIG. 12A
FIG. 12B
FIG. 12C
FIG. 12D

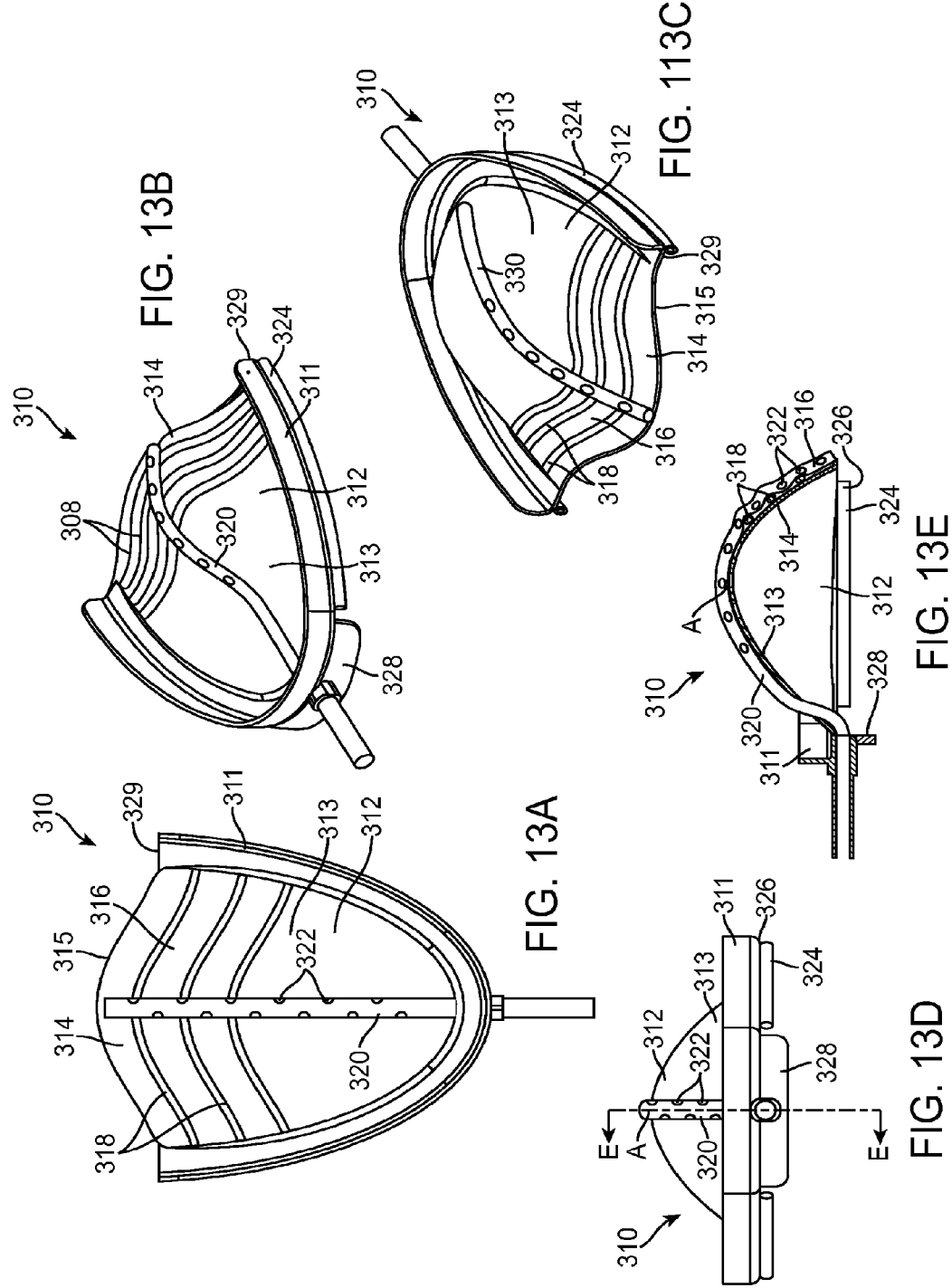

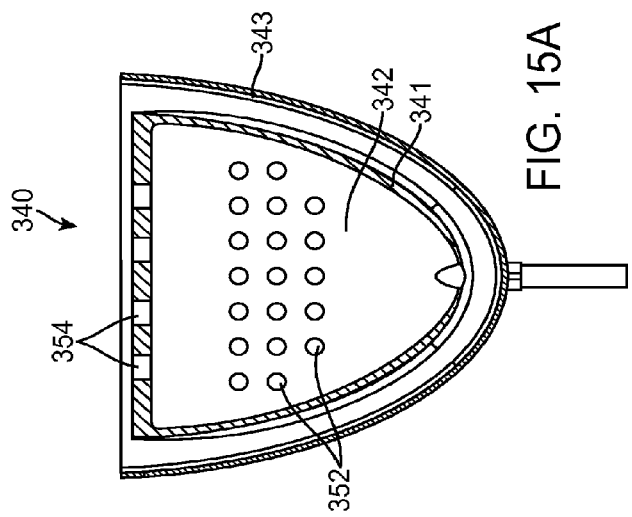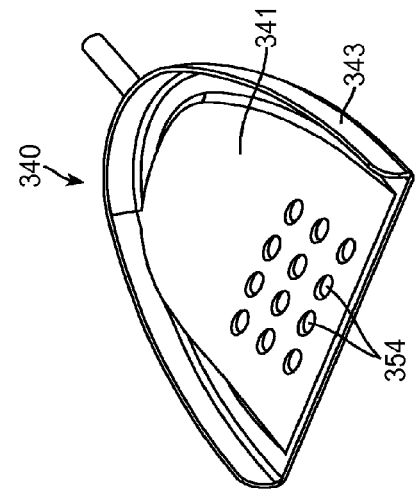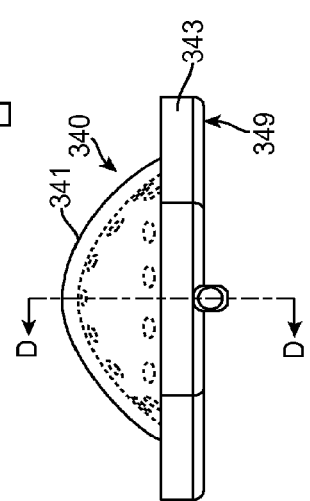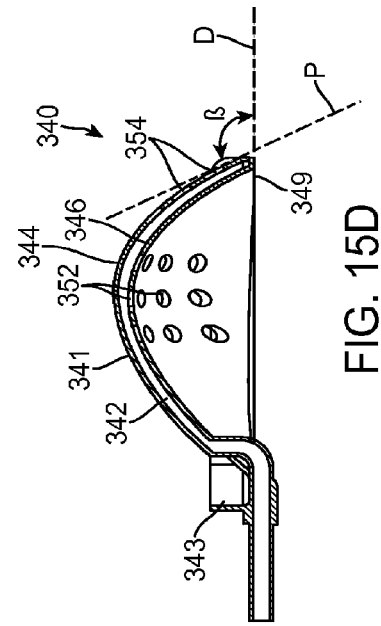

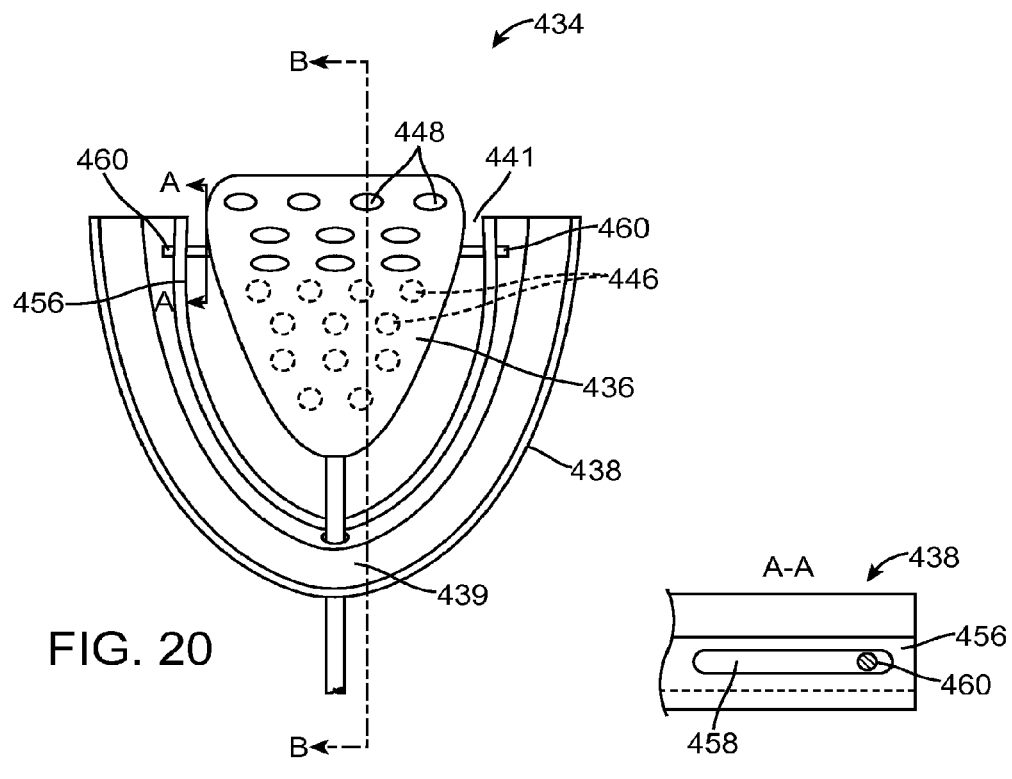
FIG. 20
FIG. 20A
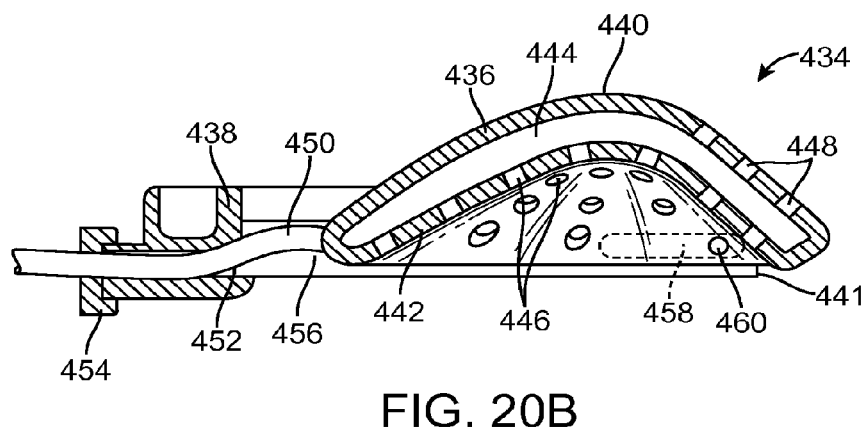
FIG. 20B

METHODS AND SYSTEMS FOR IMPROVING AIRWAY PATENCY

CROSS-REFERENCE TO RELATED APPLICATIONS

The present application is a continuation of U.S. patent application Ser. No. 13/912,021, filed Jun. 6, 2013, which is a continuation of U.S. patent application Ser. No. 12/882,054, filed on Sep. 14, 2010, now U.S. Pat. No. 8,505,540, which is a continuation-in-part of U.S. patent application Ser. No. 12/269,683, filed on Nov. 12, 2008, now U.S. Pat. No. 8,122,889, which claims the benefit of U.S. Provisional Application No. 60/987,707, filed Nov. 13, 2007, the full disclosures of which are incorporated herein by reference; U.S. patent application Ser. No. 12/882,054, filed on Sep. 14, 2010, is also a continuation-in-part of U.S. patent application Ser. No. 12/840,076, filed on Jul. 20, 2010, the full disclosures of which are incorporated herein by reference.

BACKGROUND OF THE INVENTION

1. Field of the Invention

The present invention relates generally to medical devices and methods. In particular, the present invention relates to an oral device that may be held in the mouth of a patient to reduce the incidence of obstructive sleep apnea or snoring.

Obstructive sleep apnea (OSA) is a serious medical condition resulting from a temporary airway blockage which occurs as a patient sleeps. The airway blockage usually occurs between the soft palate and/or the back of the tongue and the pharynx. As the patient breathes, the reduced area in the upper airway can cause snoring, and more seriously, OSA.

Sleep disruption caused by OSA can result in severe daytime sleepiness, chronic fatigue, headaches, depression, accidents, injuries, and of particular concern, OSA can reduce the amount of oxygen entering the lungs causing hypoxia. Hypoxia, in turn, can lead to pulmonary hypertension, heart disease, and stroke.

Numerous invasive and less invasive treatments have been proposed for OSA. Of particular interest to the present invention, "continuous positive airway pressure" (CPAP) delivers a continuous stream of pressurized air directly to the person's upper airway. The positive pressure maintains patency of the airway and inhibits the collapse associated with OSA. Although generally effective, CPAP suffers from a number of drawbacks that have led to a high level of non-compliance. The patient must wear a bulky facial mask which can be uncomfortable, and the system generates noise that can make falling asleep difficult. CPAP is also difficult to use because the mask requires careful fitting to avoid air leaks and facial discomfort and because the mask can easily be dislodged during sleep. Moreover, a number of unpleasant side effects, such as sore throats, dry throat and eyes, headaches, and skin rashes from the mask frequently occur. These problems have resulted in a high level of non-compliance with CPAP therapy.

As an improvement over CPAP, it has been proposed to apply a negative pressure to the forward end of the patient's mouth, typically at or just behind the lips, to pull the tongue forward in order to lift the rear portion of the tongue away from the back of the airway. See, for example, U.S. Patent Publication Nos. 2007/0277818, 2005/0166928 and 2005/0166929. While promising in theory, in practice it is very difficult to apply a vacuum in the region of the tip of the tongue to raise the base of the tongue and clear the patient's airway, particularly when the patient is lying on his or her back and gravity is pulling the tongue posteriorly. The tongue is a relatively large and compliant organ with significant mass, and applying a vacuum over a relatively small surface area at the tip will often not be effective in raising the back of the tongue against gravity. The moist and compliant tissues in the mouth are somewhat self-sealing, and this effect tends to inhibit the propagation of negative pressure, thereby confining the negative pressures to a relatively small area near the point of application. Thus, simply applying a vacuum at a location near the anterior tip of the tongue tends to draw the tongue up against the hard palate posterior to this location, creating a seal that restricts the propagation of vacuum through this region of contact toward the back of the oral cavity, where direct vacuum is usually required for maximum effectiveness.

As another improvement over CPAP, it has been proposed to place various devices in direct contact with the posterior tissues of the mouth such as the soft palate and posterior portions of the tongue. A major disadvantage of these approaches is that contact with certain tissues near the posterior area of the tongue may elicit the gag reflex and in any case the presence of such devices so far back in the mouth can be uncomfortable.

For these reasons, it would be desirable to provide alternative and improved methods and apparatus for treating obstructive sleep apnea and snoring. The methods and devices should be non-invasive and require no surgery or permanently implanted components. In addition, the methods and devices should be minimally intrusive with components that are comfortable and quiet so that disruption of the patient's sleep is minimized. Moreover, the methods and devices should avoid contacting the portions of the oral cavity that trigger the gag reflex. The methods and systems should also be simple to implement and be effective to significantly improve patency of a patient's airway during sleep. At least some of these objectives will be met by the inventions described hereinafter.

2. Description of the Background Art

Oral and external devices for treating sleep apnea and snoring are described in U.S. Patent Publication Nos. US2005/166929; US2005/166928; US2008/0188947; US2007/0277818; US2008/0216843; and US2008/0210244; and in U.S. Pat. Nos. 7,182,082; 7,073,506; 7,073,505; 6,955,172; 6,877,513; 6,494,209; 5,957,133; 5,465,734; 4,676,240; 4,304,227; 4,169,473; and 3,132,647; and in Cartwright and Samelson "The effects of a non-surgical treatment for obstructive sleep apnea: the tongue retaining device;" Journal of the American Medical Association 248 (1982).

BRIEF SUMMARY OF THE INVENTION

The present invention provides methods and devices for improving airway patency in patients by drawing an anterior region of the tongue upwardly (in a superior direction toward the top of the head) while simultaneously drawing the soft palate against a posterior region of the tongue. The methods typically comprise selecting a patient diagnosed with sleep apnea, where adequate diagnostic procedures are well described in the medical literature. A member is engaged across an engagement region of the patient's tongue usually located between the patient's molars sometimes referred to herein as medial region, such that the member divides the tongue into an anterior portion or segment and a posterior portion or segment. A vacuum is applied to a region between the tongue and hard palate to cause the anterior region of the tongue to rise in a superior direction. The soft palate is drawn against a region of the tongue posterior to the member. In this way, the soft palate is stabilized and sleep apnea is reduced or eliminated.

Drawing the soft palate against a region of the tongue posterior to the tongue-engaging member will seal the soft palate against the tongue to isolate the oral cavity from the patient's airway, clearing the airway for nasal breathing while stabilizing the soft palate to inhibit sleep apnea. Usually, the entire region of the tongue anterior to the tongue-engaging member will be caused to rise, and the applied vacuum will act on a superior portion of the soft palate. The vacuum may be applied through one or more vacuum ports disposed on an upper or superior surface of the tongue-engaging member, and the tongue-engaging member usually creates a clear region between a superior surface of the member and an inferior surface of the hard palate, where the clear region is preferably free of structure and usually reaches to the soft palate so that the vacuum may draw the soft palate as discussed above. Further, specific embodiments, engaging the tongue-engaging member, comprises inserting a bite structure between the patient's jaws, where the bite structure carries the engagement member. More typically, the engagement member extends across the oral cavity between left and right molars. The methods thus described may further comprise sealing the patient's lips to inhibit air from entering the oral cavity through the mouth.

The member which is engaged against the engagement region of the tongue can take a variety of configurations. Usually, the member will have an arcuate profile across the medial region of the tongue. For example, the member can be an arcuate plate extending from one side of the tongue to the other and having a depth in the anterior posterior direction in the range from 2 mm to 25 mm, usually from 4 mm to 10 mm. The plate, however, need not have an arcuate profile and can, in other cases, have a substantially flat profile across the medial region of the tongue, typically being a flat plate having depth within the dimensions set forth above. In addition to such arcuate and flat plates, the member can further comprise a hard palate engagement plate which is suspended above the tongue-engagement plate in order to engage the hard palate and help hold the tongue-engagement plate in position. In still other embodiments, the tongue-engaging member may comprise a dome-shaped tongue constraint which is placed over the tongue. The member can then be defined by a posterior edge of the dome-shaped tongue constraint which engages the engagement region of the tongue while the posterior region of the tongue may rise in a cavity or chamber formed beneath the anterior portion of the dome-shaped tongue constraint. While these tongue-engaging members are exemplary, other geometries could be utilized so long as they result in a rise in a portion of the tongue anterior to the tongue-engagement member and closure of the soft palate against a posterior region of the tongue when a vacuum is applied.

The present invention still further provides oral devices useful for performing the methods just described. An oral device according to the present invention will be intended for temporary placement in a patient's oral cavity and will comprise a base, a tongue-engaging member and a vacuum conduit. The base is adapted to be held between the patient's upper and lower teeth, and the tongue-engaging member is coupled to the base to be held in a predetermined position relative to the tongue. In particular, the tongue-engaging member will include a posterior structure that engages an engagement region of the tongue and an anterior structure that allows a tongue region anterior to the member to rise relative to the medial region when the base is held between the teeth. The oral device will further include a vacuum conduit coupled to the base and/or to the tongue-engaging member. The vacuum conduit will be configured to apply a vacuum to a region of the oral cavity posterior to the member (i.e., posterior to the engagement region of the tongue) to draw the soft palate down onto the posterior tongue.

The vacuum conduit and the oral devices of the present invention will typically be configured to draw the soft palate down onto a posterior region of the tongue. Vacuum conduits may be configured to seal the soft palate against the tongue to isolate the oral cavity from the patient's airway. The tongue-engaging members typically extend between the patient's left and right molars when the base is held between the upper and lower teeth. More typically, the base will include left and right bite structures, and the tongue-engaging member will be disposed between said left and right bite structures. In specific embodiments of the oral devices of the present invention, the tongue-engaging member will be spaced inferiorly of the hard palate when the base is held between the patient's teeth. Such positioning of the tongue-engaging member provides a clear region free from structure between the tongue-engaging member and the hard palate, where the clear region will extend all the way to the patient's soft palate. This clear region allowed the vacuum to draw the soft palate forward against the tongue as described previously. In other specific embodiments of the present invention, the vacuum conduit may be fluidly coupled to at least one vacuum port on a superior or upper surface of the tongue-engaging member. The oral device will often further comprise a lip seal coupled to the base and/or the vacuum conduit to inhibit air from entering the oral cavity through the mouth.

The anterior structure of the tongue-engaging member may have a variety of configurations. In many instances, the structure will comprise an open cavity or aperture which allows the tongue to rise therethrough without constraint. In other instances, the tongue-engaging member will comprise a dome-shaped device wherein the cavity of the dome is within the anterior structure of the member. Other tongue-engaging members were described previously with respect to the methods of the present invention.

Allowing and urging the anterior portion of the tongue to rise superiorly contributes to the ability of the device to keep the airway open. The tongue of sleep apnea patients often falls back into the airway during sleep further blocking the airway. By causing anterior portions of the tongue to rise, posterior portions of the tongue will move away from the airway to inhibit blockage of the airway. An open portion or cavity in the front of the device allows the anterior mass of the tongue to move forward and upward into a front portion of the mouth. The bite structure of the device further advances the tongue by holding the jaw open slightly create more volume in the oral cavity allowing further displacement of the tongue into the anterior region of the mouth and away from the airway. In addition to pulling the soft palate anteriorly out of the airway, the vacuum applied between the tongue-engaging member and hard palate urges the tongue into this open anterior space and away from the airway. A fully open anterior portion of the device allows the tongue to rise up and contact the hard palate so that is can maximally fill the anterior oral cavity.

BRIEF DESCRIPTION OF THE DRAWINGS

FIG. 3A is a perspective view, FIG. 3B is a top view, and FIG. 3C is a bottom view.

FIG. 6A is a perspective view, FIG. 6B is a side view, and FIG. 6C is a cross-sectional view taken along line 6C-6C of FIG. 6B.

FIG. 6D is a side cross-sectional view and FIG. 6E is a sectional view taken along line 6E-6E in FIG. 6D.

FIG. 7A is a perspective view, FIG. 7B is a detailed view of an adjustable tongue constraint, FIG. 7C is a side view of the device, and FIG. 7D is a cross-sectional view taken along lines 7D-7D of FIGS. 8A and 7C.

FIG. 9A is a perspective view, FIG. 9B is a top view, and FIG. 9C is a cross-sectional view taken along line 9C-9C of FIG. 9B.

FIGS. 12A-12D are top, oblique, front and side cross-sectional views, respectively of an oral device according to the invention in a further embodiment thereof.

FIGS. 13A-13E are top, front oblique, rear oblique, front, and side cross-sectional views, respectively, of an oral device according to the invention still another embodiment thereof, in which the lip seal is removed for clarity.

FIGS. 15A-15D are top cutaway, oblique, front, and side cross-sectional views, respectively of an oral device according to the invention in still another embodiment thereof, in which the lip seal is removed for clarity.

FIGS. 20 and 20B are top and side cross-sectional views, respectively of an oral device according to the invention in still another embodiment thereof, in which the lip seal is removed for clarity.

FIG. 20A is a side partial cross-section taken along line A-A in FIG. 20.

DETAILED DESCRIPTION OF THE INVENTION

Figure 1:
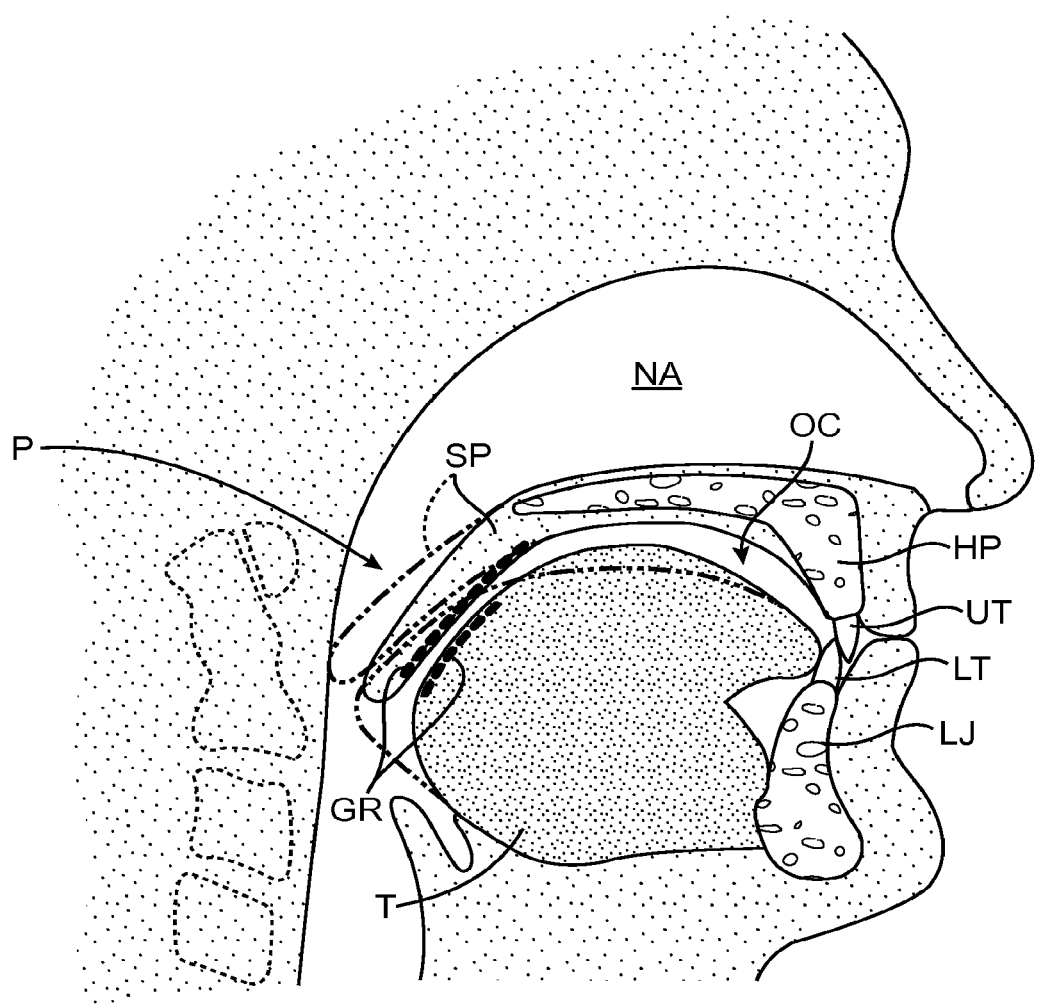
FIG. 1 illustrates the relevant anatomy of the nasal and oral cavities.

Referring to FIG. 1, the anatomy of the oral and nasal cavities relevant to obstructive sleep apnea (OSA) and the placement of the devices of the present invention will be described. The upper teeth UT of the patient are anchored in the hard palate HP, and the lower teeth LT are anchored in the lower jaw or mandible LJ. The soft palate SP extends in a rearward or posterior and inferior direction from the hard palate, and together the hard palate and soft palate divide the nasal airway NA from the oral cavity OC. The lower extent of the oral cavity is largely defined by the upper surface of the tongue T in this view, and it will be appreciated that both the soft palate SP and the tongue are mobile structures capable of movement between the positions shown in full line and broken line in FIG. 1. A nasal airway NA extends inferiorly into the pharynx P which defines the airway generally behind the soft palate SP and the tongue T. The regions on the tongue and soft palate shown with a heavy dashed line are the areas responsible for the gag reflex GR.

Obstructive sleep apnea occurs when either the soft palate, the tongue or both move in a posterior direction so that they contact the rear or posterior surface of the pharynx P. The posterior motion of the soft palate and/or tongue may also reduce the size of the airway without contacting the pharynx P causing a partial blockage. The temporary blockage of the airway behind the soft palate and tongue will cause the disrupted breathing pattern characteristic of OSA and usually associated with snoring.

Figure 2A:
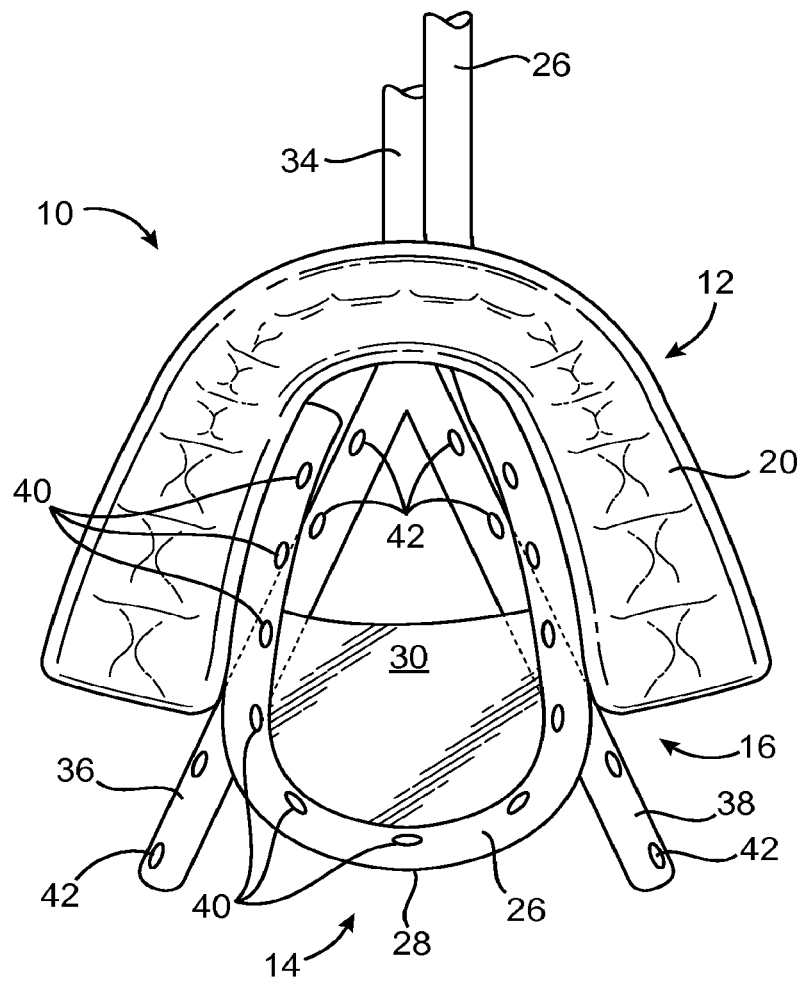
FIG. 2A illustrates a first embodiment of an oral device constructed in accordance with the principles of the present invention.
Figure 2B:
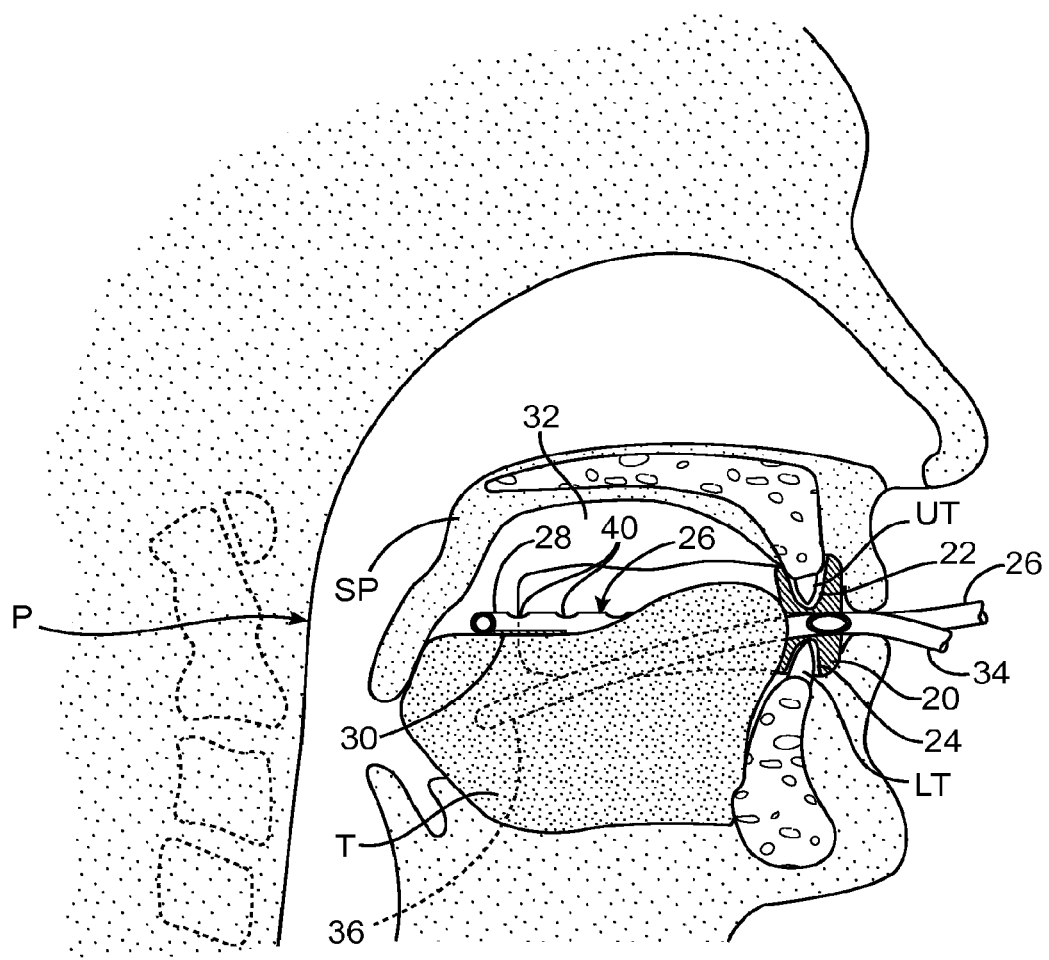
FIG. 2B illustrates use of the device of FIG. 2A for inhibition of OSA when placed in an oral cavity of a patient.

Referring now to FIGS. 2A and 2B, a first exemplary oral device 10 constructed in accordance with the principles of the present invention comprises an anchor structure 12, a tongue constraint 14, and a plenum structure 16 adapted to aspirate the oral cavity and apply a negative pressure therein while the anchor structure is held in the patient's mouth. The anchor structure 12 includes a bite structure 20 having upper and lower tooth-receiving channels 22 and 24, respectively, as best seen in FIG. 2B. The portions of upper and lower tooth-receiving channels 22 and 24 that contact the lips help to create a seal which inhibits entry of air into the oral cavity. The tongue constraint 14 comprises a J-shaped tube 26 which passes through or is otherwise coupled to the anchor structure 20 so that a posterior end 28 of the tube lies over a posterior end of the medial region of the tongue, as best seen in FIG. 2B. Optionally, the tongue constraint 14 may further include a tongue retraction plate 30 which extends over the medial region of the tongue to help constrain the tongue inferiorly to create a clear or open region 32 over the tongue and beneath the soft palate, as best seen in FIG. 2B.

The plenum structure 16 is partly formed within the J-shaped tube 26 of the tongue constraint and partly provided by a separate lateral tongue vacuum tube 34. The vacuum tube 34 has a Y-shaped geometry with legs 36 and 38 extending laterally and generally inferiorly on either side of the tongue. Legs 36 and 38 serve to create negative pressure in portions of the oral cavity that may otherwise be sealed off by the compliant mouth tissues, thereby helping to urge the tongue and soft palate forward. Both the J-shaped tube 26 and the tongue vacuum tube 34 have a plurality of vacuum ports 40 and 42, respectively, distributed along their lengths. Typically, the tubes 26 and 34 will have inside lumen diameters in the range from 0.5 mm to 5 mm, with ports having widths in the range from 0.5 mm to 10 mm, often having an oval shape as illustrated, but optionally having other shapes. By having multiple points spaced throughout the oral cavity, particularly within the posterior region of the oral cavity, the ability to provide a continuous aspiration to maintain the desired level of negative pressure or vacuum is greatly enhanced. It will be appreciated that even if certain ones of the vacuum ports 40 and 42 become blocked, others will remain open to expose the clear region created by the tongue retraction plate 30 to the desired pressure. As can be seen in FIG. 2B, vacuum tube 26, plenum structure 16, and clear region 32 provide a continuous vacuum flow path from the patient's lips to the soft palate through which vacuum may be applied. By applying the desired vacuum or negative pressure, the soft palate SP will be drawn inferiorly and anteriorly against the posterior region of the tongue T, generally forming a seal which substantially fluidly isolates the airway from the vacuum flow path and permits the negative pressure to draw the soft palate and tongue anteriorly to open up the airway behind the soft palate and tongue adjacent the pharynx P.

Figure 3A:
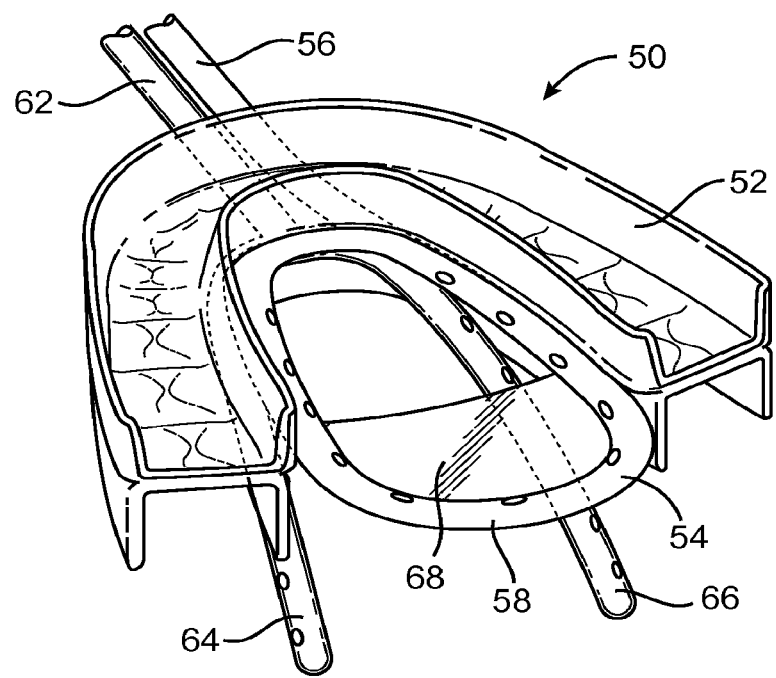
FIGS. 3A-3C illustrate a second embodiment of an oral device constructed in accordance with the principles of the present invention, where
Figure 3B:
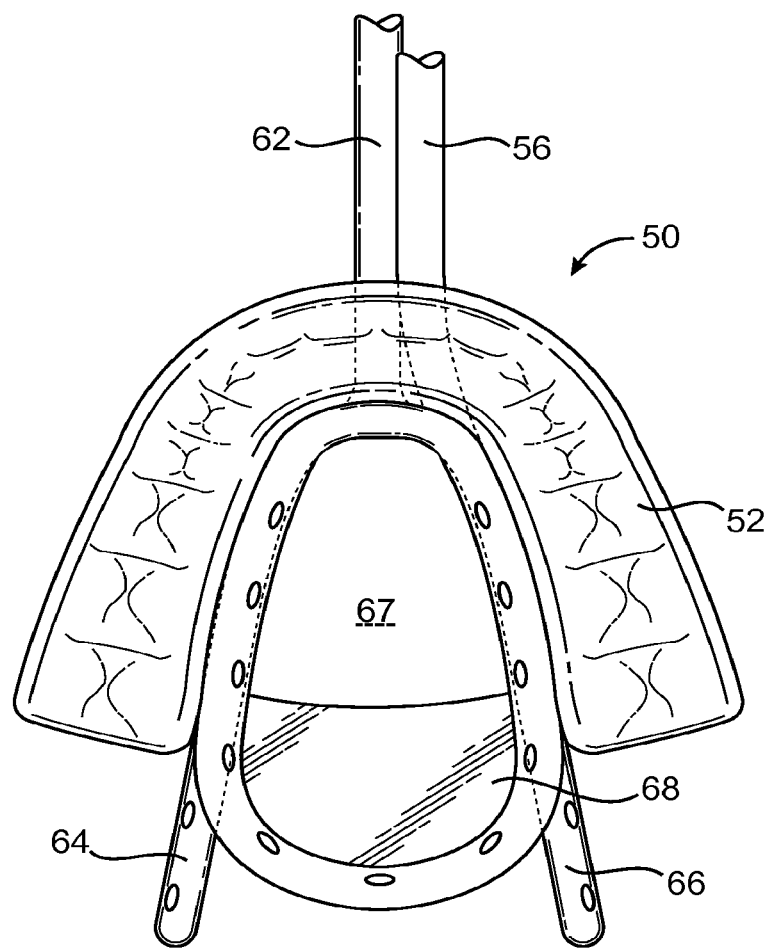
Figure 3C:
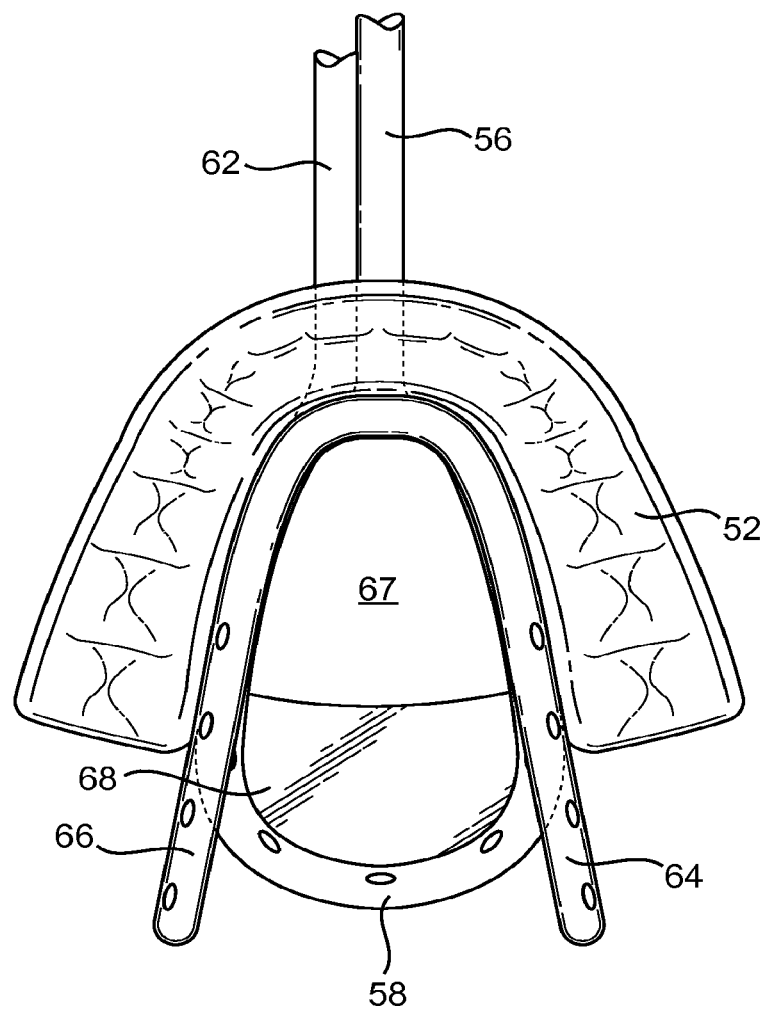

Referring now to FIGS. 3A-3C, a second exemplary embodiment of the oral device 50 will be described. The oral device 50 includes generally the same components as the oral device 10 with an anchor structure 52 being generally identical to the anchor structure 12. A tongue constraint 54 is similar to tongue constraint 14, except that it is formed from a tube 56 having an oval tubular structure 58 at its proximal end. The oval tube 58 allows the vacuum or negative pressure connection to extend through both sides of the tube, rather than terminating at one end, as with the J-shaped tube 26 of device 10. This provides for more robust operation by allowing negative pressure to be applied even if the lumen of oval tube 58 becomes clogged. Oral device 50 also includes a plenum structure comprising a tube 62 with inferiorly oriented arms 64 and 66 which is generally similar to the lateral vacuum tube structure 34 of oral device 10. The arms 64 and 66, however, are curved rather than straight as in the earlier embodiment. Oral device 50 generally provides for more open space 67 on the anterior side of the tongue refraction plate 68.

Figure 4:
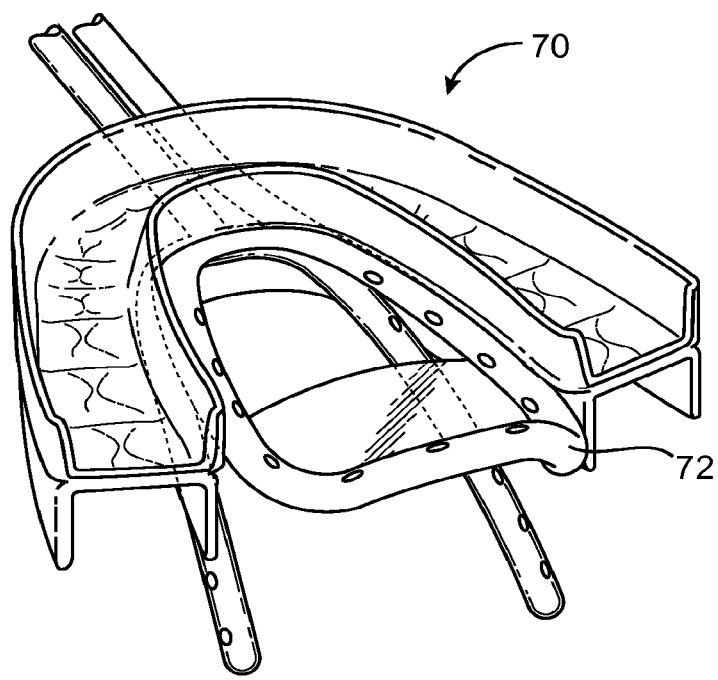
FIG. 4 is a perspective view of a third embodiment of an oral device constructed in accordance with the principles of the present invention.

FIG. 4 is a further variation of an oral device 70 which is almost identical to device 50, except that a tongue constraint structure 72 has an arcuate or curved lateral cross section in contrast to the straight cross section of tongue constraints 54 and 14 in oral devices 50 and 10, respectively. The arcuate shape of the tongue constraint structure 72 may improve the comfort of the device by allowing for a more natural tongue position. The palate and the tongue naturally take on a similar domed shape.

Figure 5:
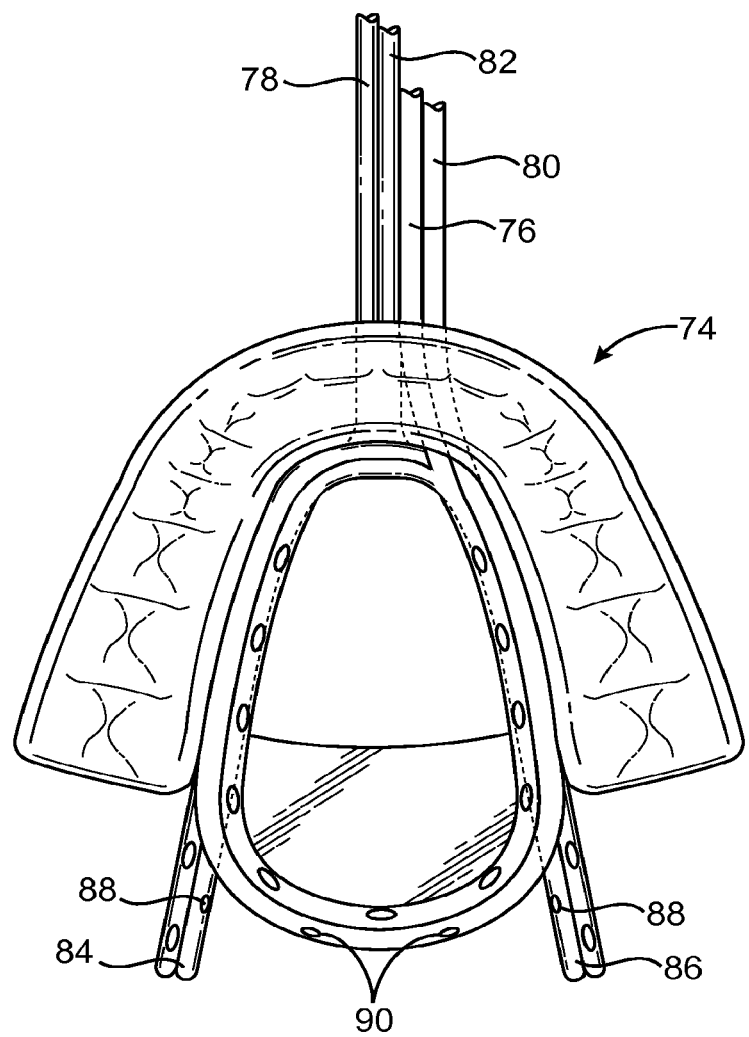
FIG. 5 is a top view of a fourth embodiment of an oral device constructed in accordance with the principles of the present invention.
Figure 6A:
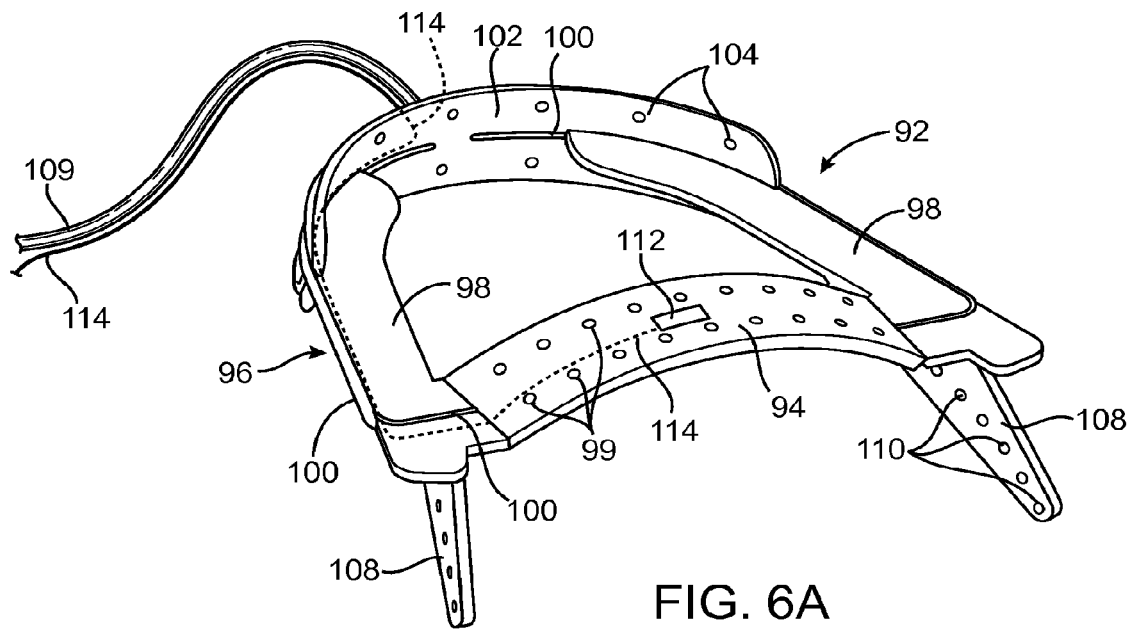
FIGS. 6A-6C illustrate a fifth embodiment of an oral device constructed in accordance with the principles of the present invention, where
Figure 6B:
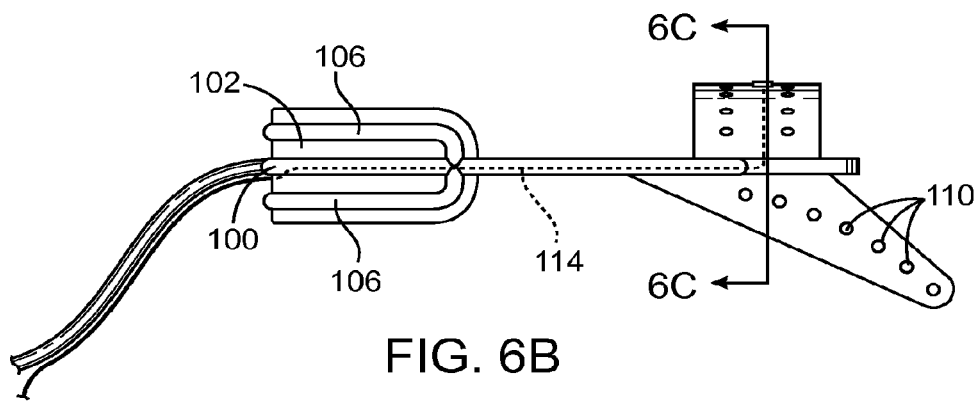
Figure 6C:
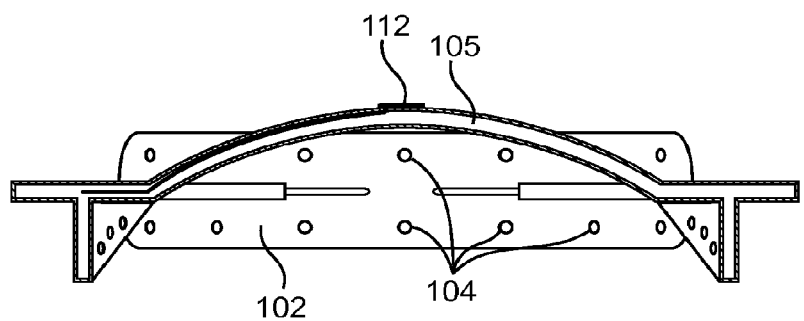
Figure 6D:
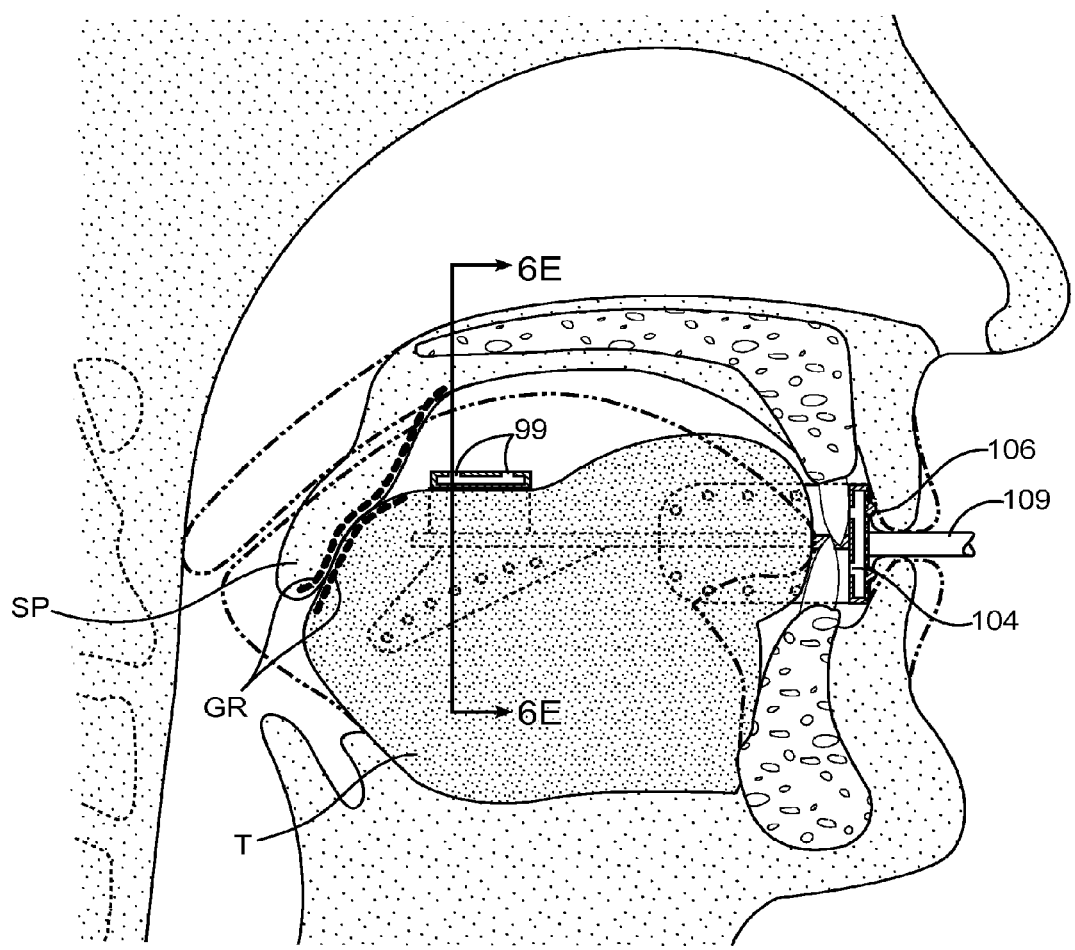
FIGS. 6D and 6E illustrate use of the device of FIGS. 6A-6C for inhibiting OSA when placed in an oral cavity of a patient, where
Figure 6E:
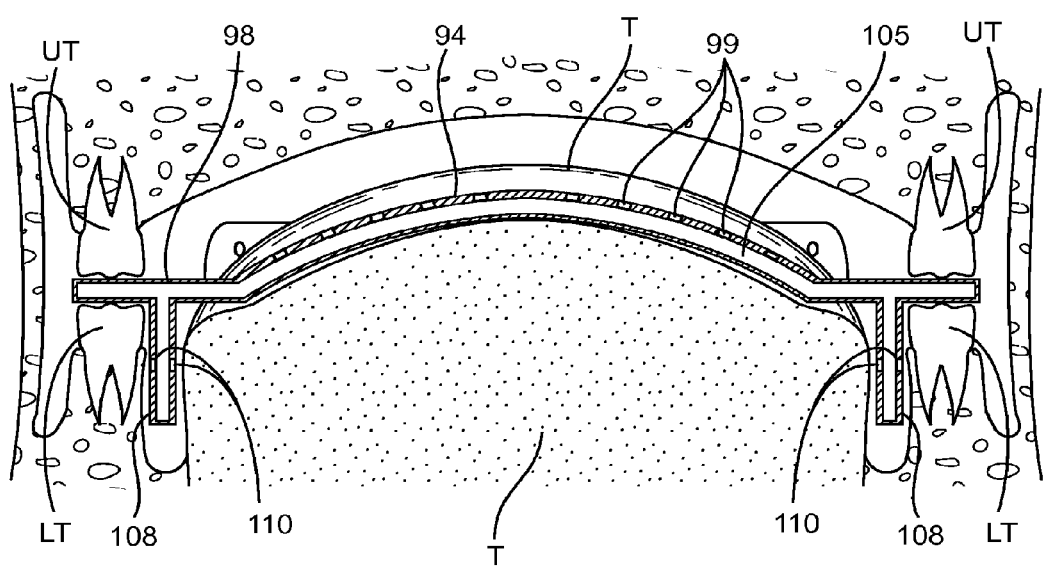

FIG. 5 is a further variation of an oral device 74 which is almost identical to device 50 with tube 76 being generally identical to tube 56 and tube 78 generally being identical to tube 62. Oral device 74 also includes tubes 80 and 82 which generally follow the paths of tubes 76 and 78, respectively. Tube 82 bifurcates into arms 84 and 86 in a similar manner as arms 64 and 66. Ports 88 and 90 are in fluid communication with tubes 82 and 80, respectively. Tubes 80 and 82 can be thereby be used to monitor the negative pressure in the oral cavity at the locations of ports 88 and 90 by connecting tubes 80 and 82 to pressure sensors. In addition fluids such as humid air or warmed saline may be introduced via tubes 80 and 82 and ports 88 and 90 in order to enhance patient comfort by moistening the oral cavity or by helping to aspirate fluids such as saliva that may have collected in the oral cavity.

Referring now to FIGS. 6A-6E, a third exemplary embodiment of the oral device 92 will be described. The oral device 92 generally provides similar components as the oral device 70. An anchor structure 96 includes bite structure 98 which is configured to be held between the patient's upper and lower teeth. Bite structure 98 does not include tooth-receiving channels and is open at the front allowing the front teeth to overlap, thus improving patient comfort by minimizing the bulk of the device and allowing the mouth to close more than oral device 70 allows. Instead of relying on tubes to convey the negative pressure, tongue constraint structure 94 is hollow and includes one or more vacuum ports 99, thereby reducing the overall size and bulk of the tongue constraint structure. Portions of bite structure 98 may be hollow and used to convey the negative pressure. A tubular structure 100 may additionally be employed to convey the negative pressure. A lip seal structure 102 facilitates creating a seal at the mouth by contacting the inner surface of the lips proximate the mouth opening. The lip seal structure 102 may also be hollow in order to convey negative pressure to vacuum ports 104 which are positioned to help ensure that negative pressure is well-distributed proximate the lips, thus providing for improved lip sealing forces. One or more lateral tongue structures 108 may be flexible and also hollow in order to convey negative pressure to vacuum ports 110 which are positioned to enhance the distribution of negative pressure into the oral spaces lateral to the tongue. A vacuum plenum 105 may thusly comprise contiguous hollow portions of lip seal structure 102, tubular structure 100, bite structure 98, tongue constraint structure 94, lateral tongue structures 108, and a vacuum tube 109 that is connected to a source of negative pressure. Optionally, lip seal protrusion 106 may enhance the formation of a seal at the lips by concentrating lip contact forces at the protrusion. Optionally, a sensor 112 such as a pressure sensor with connecting cable 114 may be mounted on tongue constraint structure 94 or on any other part of the device for example to monitor the pressures developed in the oral cavity.

Figure 7A:
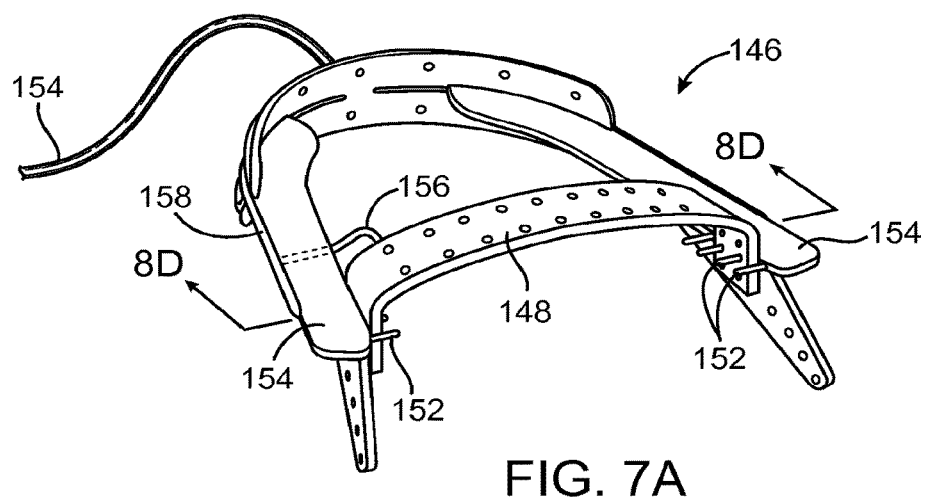
FIGS. 7A-7D illustrate a further embodiment of an oral device constructed in accordance with the principles of the present invention, where
Figure 7B:
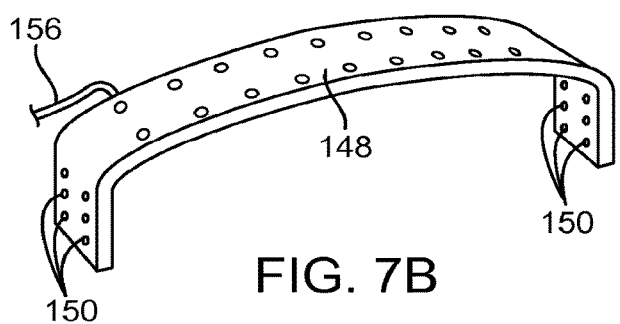
Figure 7C:
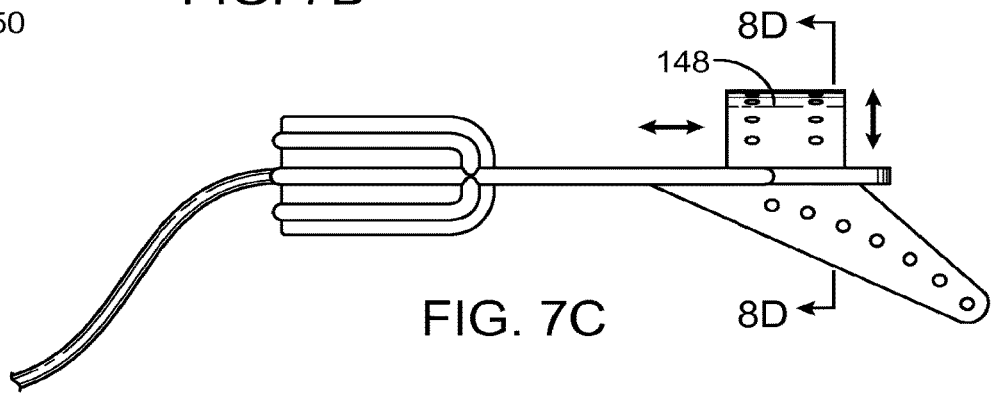
Figure 7D:
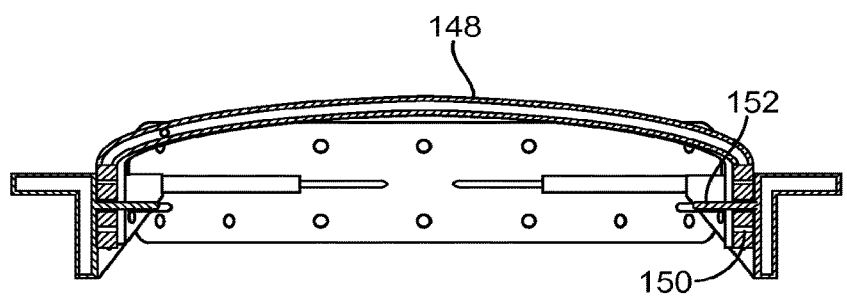

Referring now to FIGS. 7A-7D, an oral device 146 which is very similar to oral device 92 except that it employs an adjustable tongue constraint structure 148 which can be used with any of the oral devices described is illustrated. Adjustable tongue constraint structure 148 has three pairs of through holes 150 at each side. Each pair of through holes 150 may be engaged with a pair of the four protrusions 152 which extend from each of the bite structures 154. It can be appreciated that adjustable tongue constraint structure 148 may be moved superiorly, inferiorly, anteriorly, and posteriorly by engaging various pairs of holes 150 with appropriate pairs of protrusions 152 as best shown in FIG. 7A. Such adjustability facilitates the fitting of oral device 146 to the anatomy of a particular patient. Adjustable tongue constraint structure 148 is hollow and is connected to vacuum tube 154 by means of flexible tube 156 and tubular structure 158. Bite structures 154 may also be hollow in order to convey negative pressure as with oral device 92.

Figure 8A:
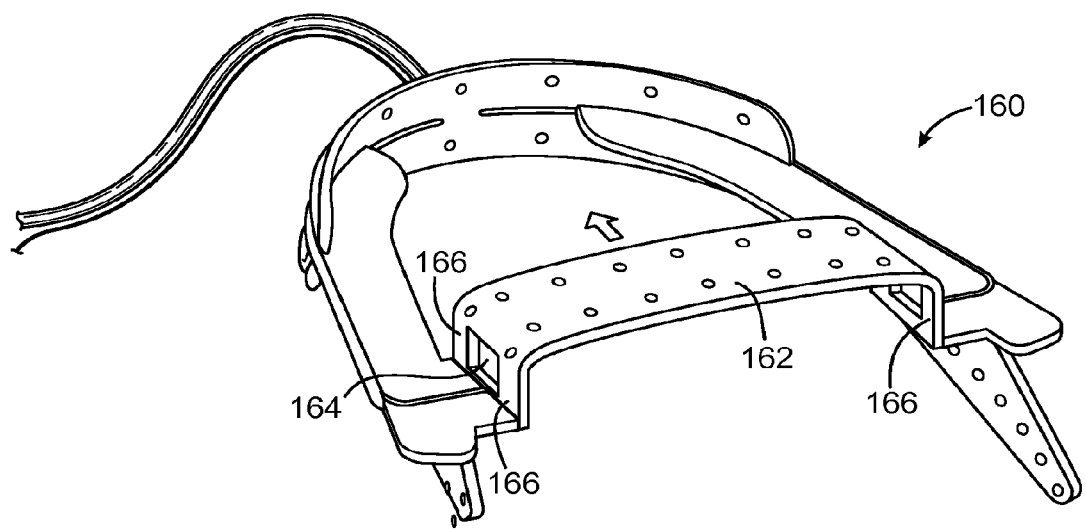
FIGS. 8A-8C illustrate yet another embodiment of an oral device constructed in accordance with the principles of the present invention, with FIG. 8A being an perspective view, FIG. 8B being a side view, and FIG. 8C being a cross-sectional view taken along line 8C-8C of FIG. 8B.
Figure 8B:
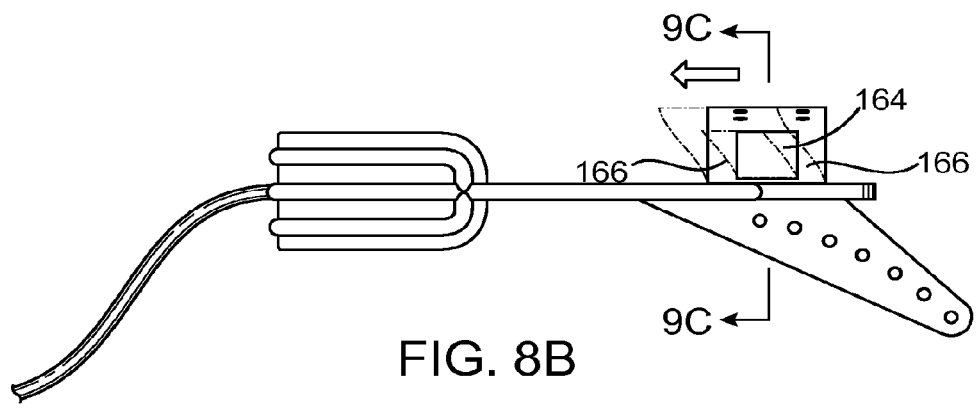
Figure 8C:
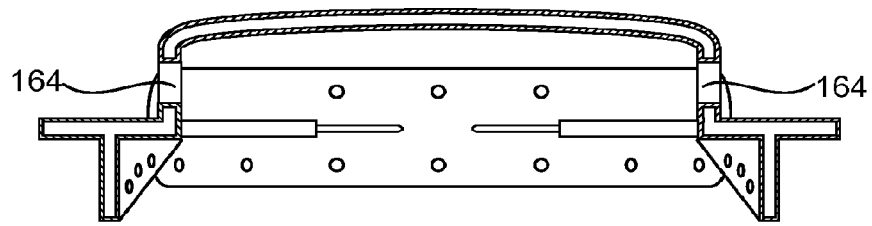

Referring now to FIGS. 8A-8C, an oral device 160 which is very similar to oral device 92 except that it employs a flexing tongue constraint structure 162 which can be used with any of the oral devices described is illustrated. Flexing tongue constraint structure 162 is very similar to tongue constraint structure 94 except that a window 164 is formed at each lateral end of the flexing tongue constraint structure 162. Windows 164 are sized to create a pair of narrow flexure arms 166 at each lateral end of flexing tongue constraint structure 162. Flexure arms 166 are fabricated from a flexible material such as polyurethane so that flexing tongue constraint structure 162 is allowed to flex anteriorly when the portion of the tongue it contacts is urged anteriorly by the negative pressure in the oral cavity. This anterior motion of flexing tongue constraint structure 162, best seen in FIG. 9B, may facilitate further anterior motion of the tongue and soft palate as compared with oral device 92, thereby improving the ability of oral device 160 to open the airway. Because flexing tongue constraint structure 162 and flexure arms 166 are hollow, negative pressures are conveyed in a very similar manner as with oral device 92.

Figure 9A:
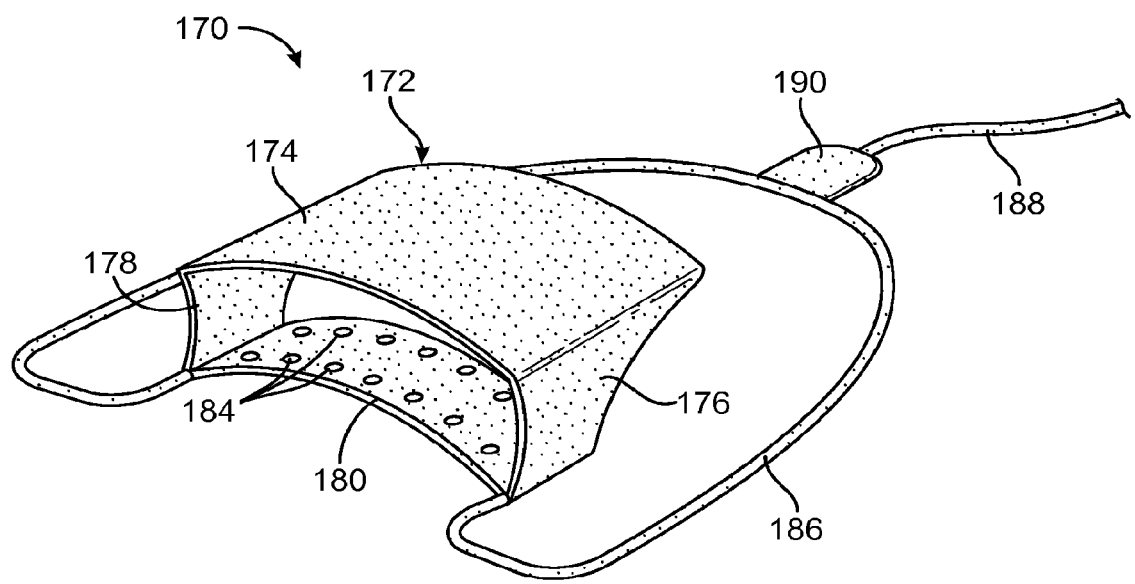
FIGS. 9A-9C illustrate still another embodiment of an oral device constructed in accordance with the principles of the present invention, where
Figure 9B:
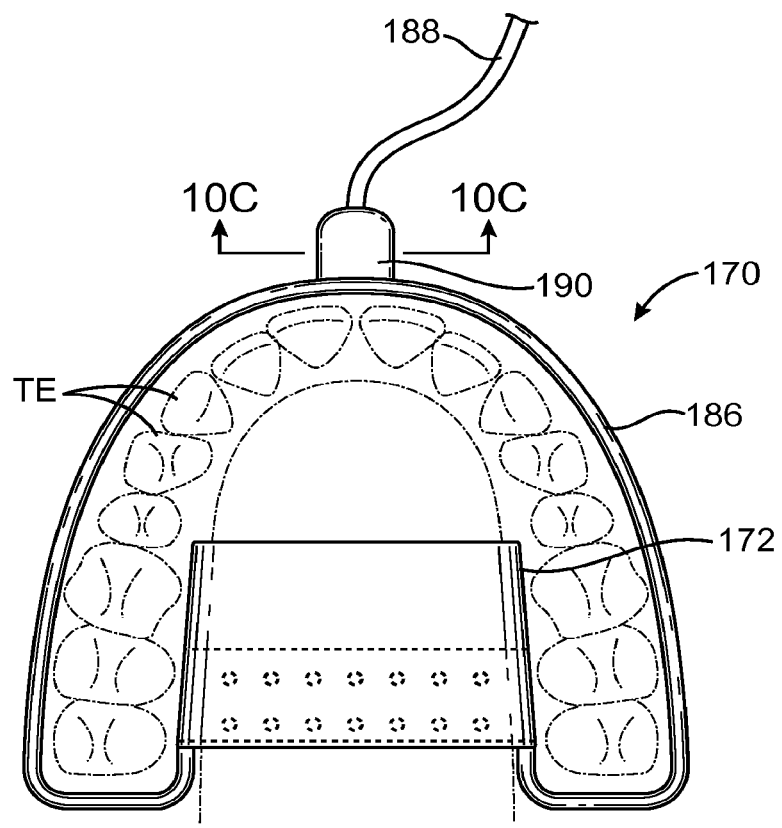
Figure 9C:
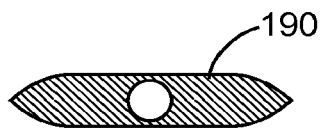
Figure 9D:
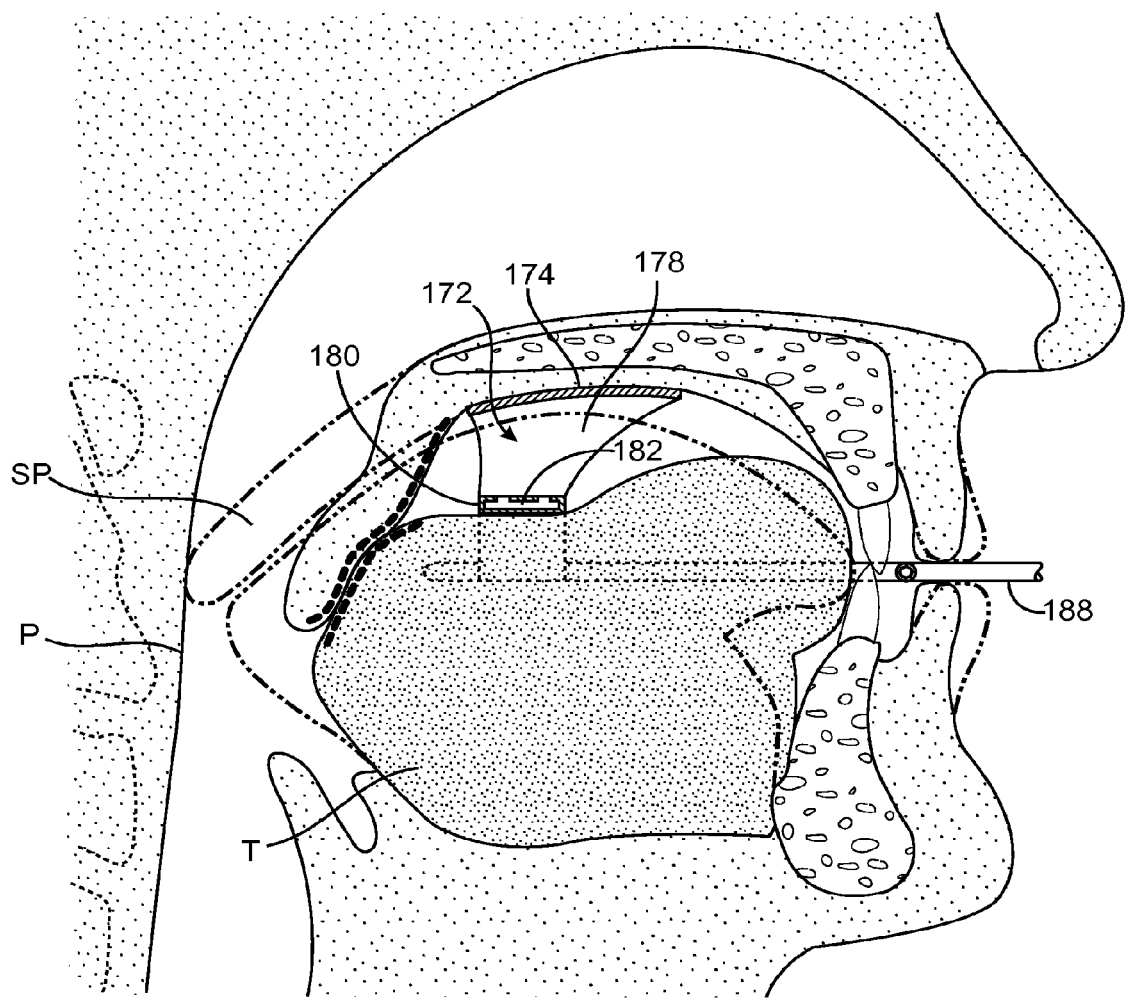
FIG. 9D illustrates use of the device of FIGS. 9A-9C for inhibiting OSA when placed in an oral cavity of a patient.

Referring now to FIGS. 9A-9D, an oral device 170 having an alternative anchor structure 172 will be described. In all previous embodiments, the anchor structure of the oral device has been intended to be held between the patient's teeth in order to provide a support for the tongue constraint. That is, the anchor structure held between the patient's teeth is attached to the tongue constraint and transmits force to maintain the tongue position through the anchor between the teeth. In the oral device 170, the anchor structure 172 has an upper surface 174 which is configured to rest against the inferior surface of the palate, as best seen in FIG. 9D. A pair of depending sidewalls 176 and 178 adjoin to a curved or arcuate tongue constraint 180 which includes an open interior or plenum 182 having a plurality of ports 184 over its upper surface.

Vacuum or negative pressure can be provided to the plenum 182 by a U-shaped tube 186 which is adapted to circumscribe the patient's teeth TE, as best shown in FIG. 9B. It can be seen that the teeth can be fully closed with the tube extending around the rear molars when the anchor structure 172 is positioned in the oral cavity, as shown in FIG. 9D. A flexible tube 188 is connected to the vacuum supply tube 186 through a lip seal structure 190, as shown in cross section in FIG. 9C. The lip seal structure 190 has a flat and tapered shape so the patient's upper and lower lips can conform to it thereby facilitating the seal in the oral cavity as a vacuum or negative pressure is drawn through the device.

Figure 10:
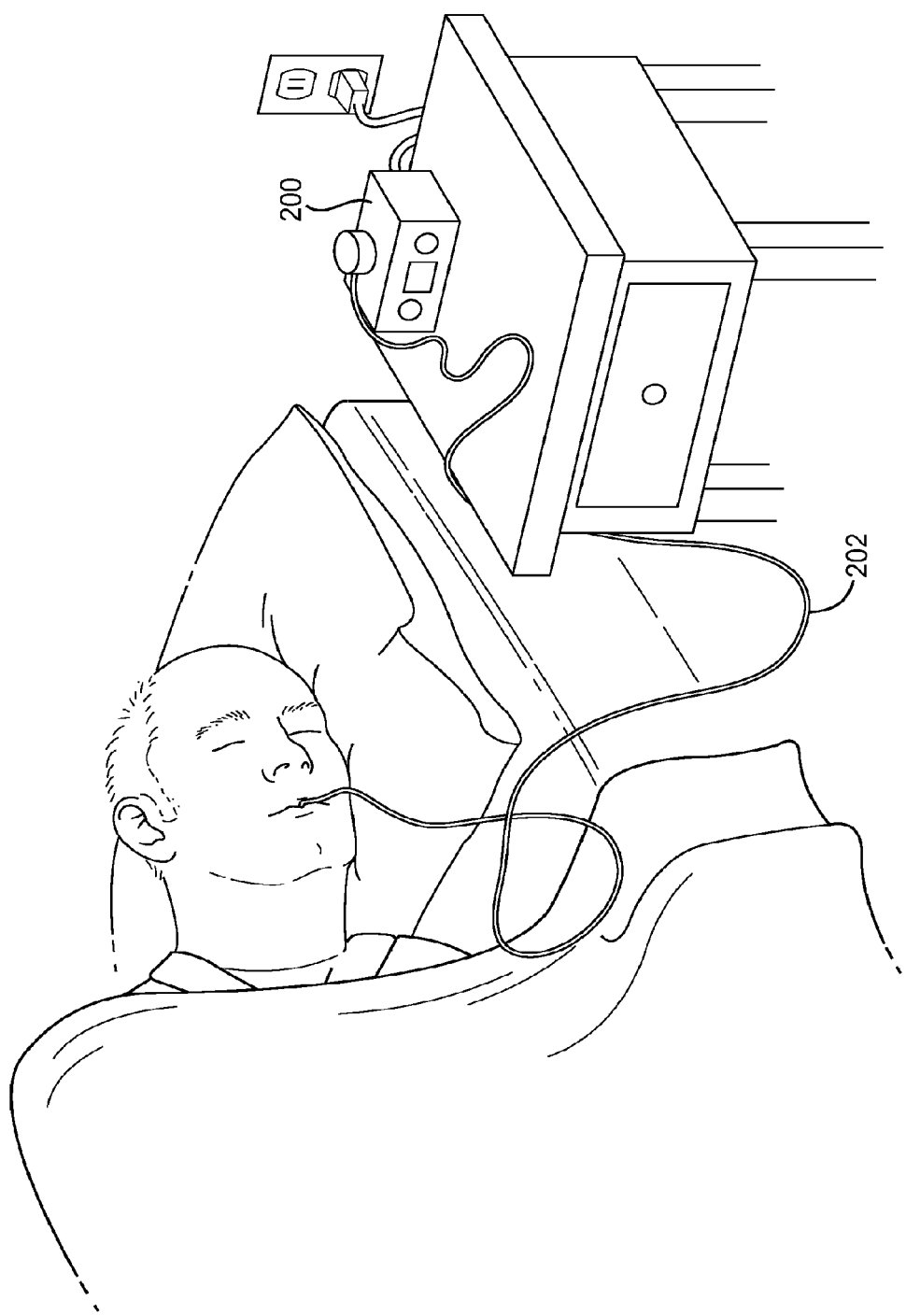
FIG. 10 is a perspective view illustrating a patient asleep at night using the apparatus of the present invention.

Referring now to FIG. 10, in addition to the portable battery powered vacuum source described earlier, the oral devices of the present invention may receive the desired vacuum or negative pressure from a tabletop unit 200 which can be operated off of house current and/or battery power. The tabletop unit 200 may be connected to the oral device (within the patient's mouth in FIG. 10) through a relatively long, flexible, crush-resistant, small and lightweight connector tube 202. The long connector tube is convenient and allows the patient to sleep comfortably in any position with minimal disruption.

Figure 11:
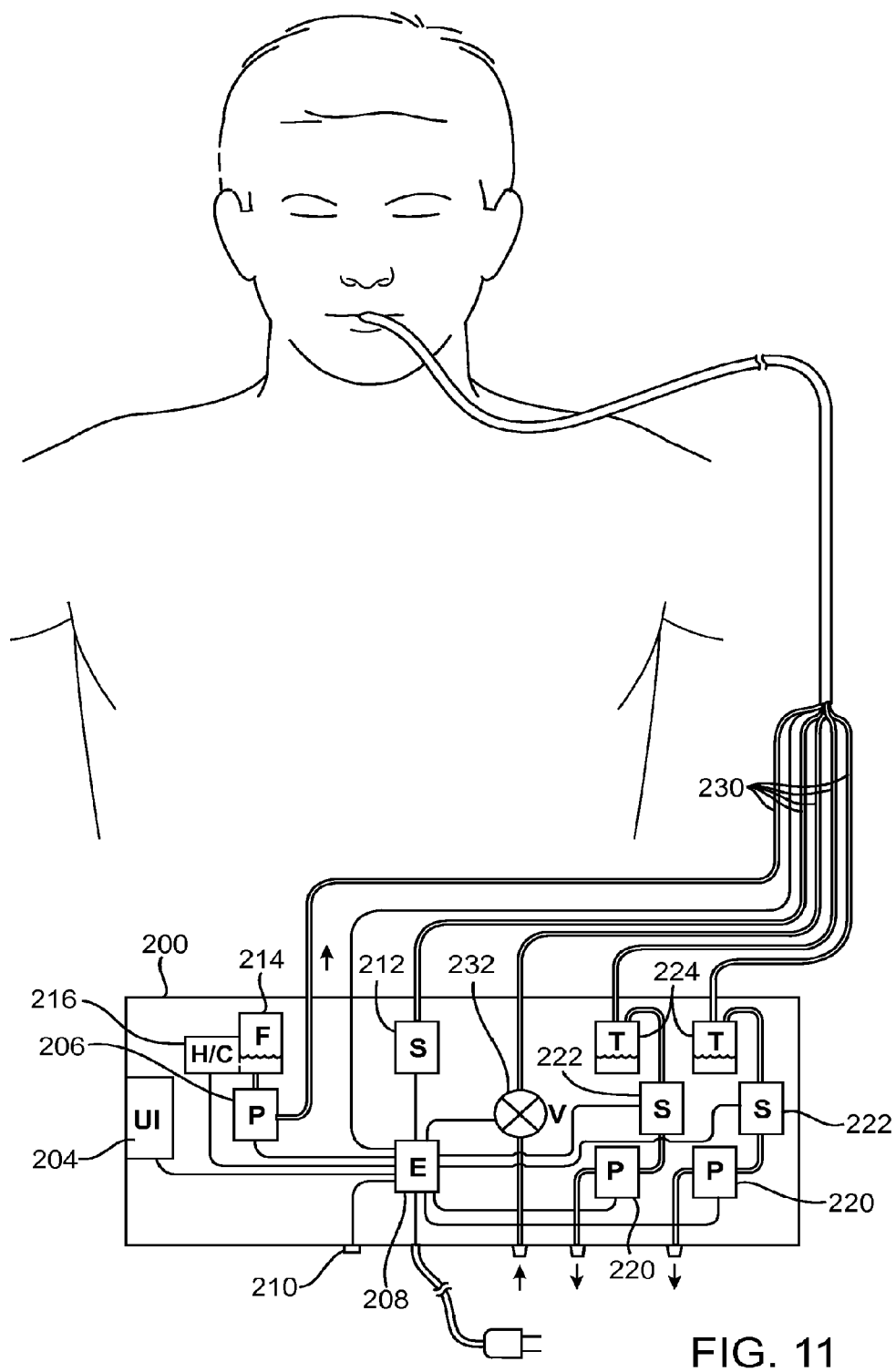
FIG. 11 is a schematic illustration of a control system or console for use in aspirating a negative pressure in the oral devices of the present invention.

The tabletop control unit 200 may comprise a number of internal components, as best illustrated in FIG. 11. The tabletop control unit will usually include a user interface 204. In order to generate the negative pressure used by the oral devices described above and to reduce the accumulation of fluid within the mouth, one or more pumps 220, sensors 222 for flow, pressure, or the like and traps 224 will usually be provided. The traps 224 remove saliva and other substances from the tubing to prevent them from entering the pumps 220. The sensors 222 may be used to determine if the device is operating and being applied properly. For example an air leak would generate higher than normal flow and the user could be alerted that there is a problem. Optionally valve 232 may be provided for briefly allowing air to enter the device or oral cavity in order to facilitate aspiration of fluids that have collected in the oral cavity or device. Optionally fluid source 214 and pump 206 for providing moisture and a heater/cooler 216 for heating or cooling the fluid, may be provided. Electronics and power control module 208 will provide for the desired control functions of the unit. Optionally a feedback loop may be configured to monitor the pressure in the oral cavity for example as described above using tubes 80 and 82 connected to a pressure sensor 212 and to adjust the power of the one or more vacuum pumps 220 in order to maintain the desired level of negative pressure in the oral cavity. Varying distributions of saliva in the tubing that connects the control unit 200 to the oral devices described above will create a pressure differential and such a feedback loop could continually compensate for this varying differential. Optionally, a port 210 may be provided for external connection of the control unit to a computer or data distribution network. Each of these components may be connected to the oral device through appropriate tubes, wires or other connectors 230.

A further embodiment of an oral device according to the invention is illustrated in FIGS. 12A-D. Oral device 280 has a tongue constraint 282 with a bite structure 284 integrally formed with or fixed to the tongue constraint 282 around its anterior and lateral edges. Similar to previous embodiments, bite structure 284 has a U-shaped channel 286 adapted to receive the upper teeth so as to anchor the oral device 280 in the oral cavity. U-shaped channel has an outer wall 287 which extends superiorly to cover at least a portion of the upper teeth, and an inner wall 289 which may be shorter or optionally eliminated entirely. Outer wall 287 and/or inner way 289 may have a height to cover the upper teeth entirely so as to inhibit leaks from the oral cavity posterior to the teeth.

Tongue constraint 282 comprises a curved or dome-shaped plate 288 having a concave inferior surface adapted to engage the superior surface of the tongue to constrain at least a portion of the tongue in a position spaced apart from the patient's hard palate, thereby creating a clear region superior to plate 288 and inferior to the hard palate that continuously extends from the posterior side of bite structure 284 to the soft palate. In preferred embodiments, the superior surface of tongue constraint 282 is spaced apart from the patient's hard palate by at least about 0.5 mm. Tongue constraint 282 preferably has sufficient rigidity to constrain the tongue in a position-spaced apart from the hard palate. While some flexibility is possible, tongue constraint 282 will have sufficient resilience and strength to overcome any deflection caused by movement of the tongue to return to an unbiased position in which the tongue is spaced apart from the hard palate. In order to apply a distributed force across a broad area of the tongue, tongue constraint 282 is preferably configured to engage at least ½ of the width of the tongue (in the lateral direction, left to right). In this embodiment, plate 288 of tongue constraint 282 spans the entire distance across the open end of U-shaped bite structure 284 between the patient's left and right molars and is thus configured to engage substantially the entire width of the tongue.

As in previous embodiments, the plate 288 preferably engages the medial region of the tongue so as not to contact the region of the tongue that tends to initiate the gag reflex. Plate 288 is preferably continuous throughout the area circumscribed by bite structure 284 (except for vacuum ports 296, described below). Plate 288 will usually engage the medial surface of the tongue at a location that is at least about ⅓ of the way, more preferably at least about ½ of the way, from the anterior tip of the tongue to the posterior end of the tongue. Usually, plate 288 engages the medial surface at a point posterior to the midpoint between the anterior and posterior ends of the hard palate. Plate 288 may engage the tongue as far back as or even beyond the posterior end of the hard palate where it joins to the soft palate; however, plate 288 is configured to allow the soft palate to engage the posterior side of plate 288 in a position in which the airway is at least partially open, so will usually not extend posteriorly more than about 20 mm beyond the posterior end of the hard palate HP, and preferably not more than about 25 mm posteriorly beyond the normal location of the patient's second molars. If an imaginary cylinder were drawn between the patient's nasopharynx and laryngopharynx with diameter about the same as the laryngopharynx, in preferred embodiments plate 288 would not intersect such a cylinder.

Plate 288 forms a soft palate landing pad 290 on its posterior side having a posterior surface 292 which angles inferiorly and posteriorly from the apex A of the dome-shaped plate 288. Soft palate landing pad 290 is adapted to engage the soft palate when vacuum is applied through the oral device. Posterior surface 292 may be arcuate, spherical, planar or a combination thereof. In exemplary embodiments, as shown in FIG. 12D, posterior surface 292 extends a length L of at least about 5 mm from the inferior surface 295 of bite structure 284, and posterior surface 292, or a plane P tangential with posterior surface 292, is disposed at an angle a of at least about 45°, more preferably about 60-135°, and most preferably about 90-135°, relative to a horizontal plane H containing an inferior surface 295 of the bite structure 284. Horizontal plane H is generally coplanar with the occlusal plane, the plane in which the upper and lower teeth meet when the patient bites together.

Plate 288 has a plurality of vacuum ports 296 extending entirely through its thickness. Vacuum ports 296 are disposed in locations on plate 288 selected to direct negative pressure (suction) within the clear region superior to plate 288 against the superior surface of the tongue on the inferior side of plate 288. Various locations and arrangements are possible, but in one embodiment vacuum ports 296 are disposed within a central region of plate 288 which contacts the medial region of the tongue. In this embodiment vacuum ports 296 are arranged in a grid generally centered on apex A in a central portion of plate 288 and extending laterally in both directions to points adjacent to U-shaped channel 286, with soft palate landing pad being free of vacuum ports. Optionally, vacuum ports 296 may also be provided on soft palate landing pad 290.

As an alternative to vacuum ports 296 shown, plate 288 may be made of a porous material to allow air to pass through it, such as a porous polyethylene or other porous polymer. As a further alternative, plate 288 may have very small or even microscopic holes created by laser drilling, etching, or other suitable process throughout its entire area or in a selected region or regions thereof.

A vacuum tube 298 is fixed to the surface of plate 288 and extends anteriorly through plate 288 and bite structure 284 where it connects to an extension tube 300, which is connectable to a suction source such as a vacuum pump or portable vacuum source as described in earlier embodiments. Optionally, a detachable connector (not shown) may be connected to the end of extension tube 300 to allow detachable connection to a complementary connector (not shown) on a portable vacuum source or a tube extending to the vacuum source. Vacuum tube 298 preferably has a plurality of holes 302 on a sidewall thereof, and may have an open distal end 304, through which vacuum is applied to the clear space created superiorly of plate 288. Vacuum tube 298 may be straight and located in the center of plate 288 as shown, or alternatively may have a variety of other configurations and locations on the oral device as described elsewhere herein. Vacuum tube 298 may terminate at a point anterior to apex A as illustrated, or may extend to a point further posterior on the plate 288. As an alternative to the vacuum tube 298 illustrated, a vacuum lumen may be formed integrally within plate 288 with outlet ports in the superior surface and/or inferior surface of plate 288 in communication with the vacuum lumen.

Oral device 280 further includes a lip seal 306 configured to be placed between the teeth and lips to help inhibit air from leaking between the lips so as to maintain a seal in the oral cavity. Lip seal 306 may comprise a flexible polymeric sheet slidably mounted over extension tube 300 and fluidly sealed therewith. Lip seal 306 will have sufficient flexibility to conform to the shape of the user's teeth and lips so as to provide a substantially air-tight seal.

Figure 12E:
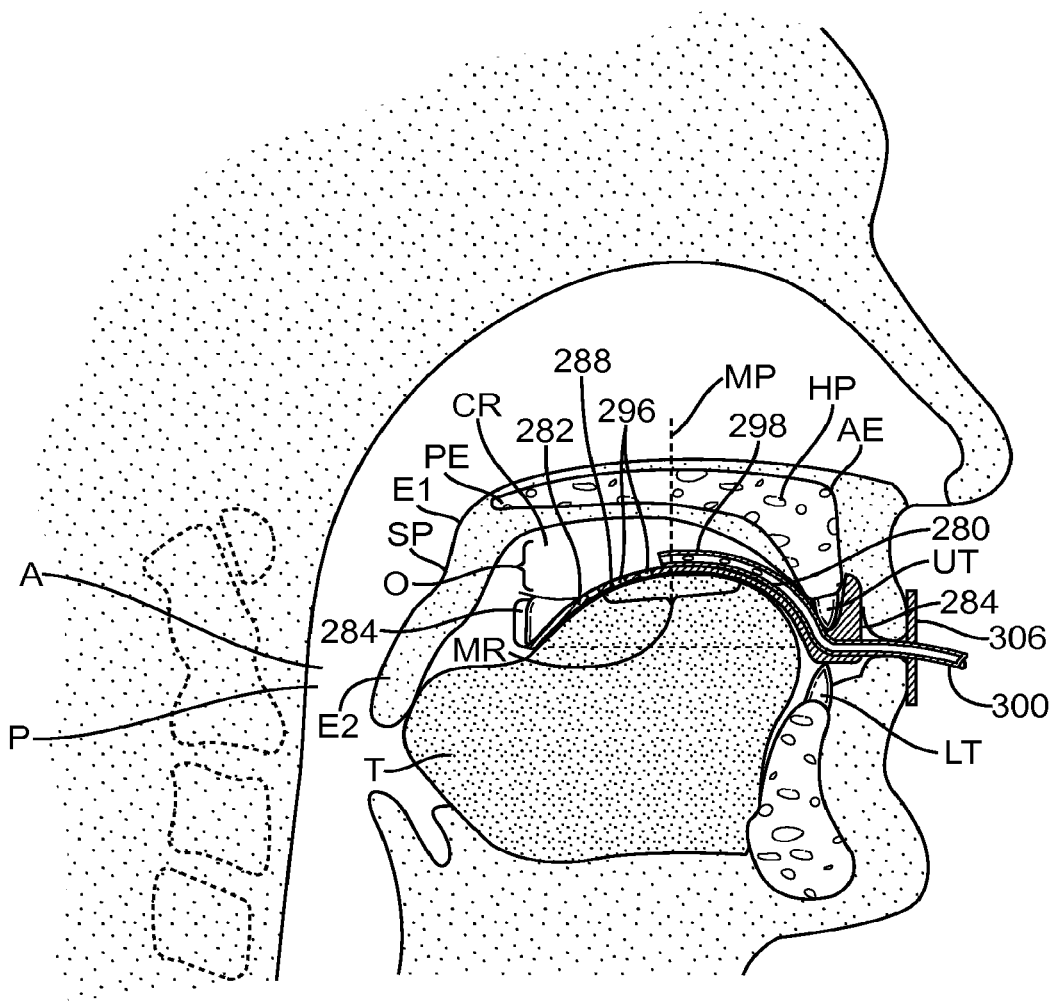
FIG. 12E is a side cross-sectional view of the oral device of FIGS. 12A-D positioned in a patient's oral cavity.

Referring to FIG. 12E, tongue constraint 282 preferably engages and constrains a region of the tongue T which is at least in part posterior to the midpoint MP between the anterior end AE and the posterior end PE of hard palate HP. In the embodiment shown, tongue constraint 282 extends in the posterior direction substantially the entire distance from the anterior end AE to the posterior end PE of hard palate HP, thus engaging both a medial region MR of the tongue T (roughly the middle third) as well as regions of the tongue anterior and posterior to the medial region MR Tongue constraint 282 creates a posterior opening 0 bounded superiorly by the hard palate, laterally by the teeth and bite structure 284, and inferiorly by the posterior edge of plate 288. This posterior opening faces directly toward the soft palate SP and airway A, creating a vacuum flow path from the clear region CR directly to the soft palate. This allows vacuum to be applied to at least the upper portion of the soft palate SP, from the superior end E1 where it joins the hard palate to a point closer the free inferior tip E2. Exerting vacuum force on the superior portion of the soft palate effectively maintains the entire soft palate structure in a position in which the airway is unobstructed.

In use, vacuum applied through vacuum tube 298 is directed to the tongue T through vacuum ports 296 and holds the tongue in engagement with the inferior surface of plate 288. Although some or all of vacuum ports 296 may be blocked by the tongue, because the clear region maintained over oral device 280 is open posteriorly all the way to the soft palate, a vacuum flow path is maintained from vacuum tube 298 directly to the soft palate. Thus the negative pressure within the clear region exerts a force directly upon the soft palate through this vacuum flow path, maintaining the soft palate in an anterior position in which it does not obstruct the airway. Preferably, the suction force exerted on the soft palate through the clear region maintains the soft palate in sealing engagement with the tongue and/or with the soft palate landing pad 290, while the tongue is held in engagement with the inferior surface of the tongue restraint 282. This allows the airway to be substantially fluidly isolated from clear space CR where the vacuum is applied such that the pressure gradient between the airway and the oral cavity increases, thus urging the soft palate, tongue and other posterior oral tissues anteriorly out of the airway.

Still another embodiment of an oral device according to the invention is illustrated in FIGS. 13A-E. In this embodiment, oral device 310 is identical to oral device 280 of FIGS. 12A-D except as described below. Oral device 310 has a bite structure 311 like that of the previous embodiment, and a tongue constraint 312 comprising a plate 313 with a soft palate landing pad 314. Unlike the straight posterior edge of landing pad 290 in the previous embodiment, landing pad 314 has a posterior edge 315 with an arcuate shape that curves outwardly in the posterior and (optionally) inferior directions beyond the open end of bite structure 311. With this shape landing pad 314 may be more suitably located to engage the soft palate in some patients. In addition, landing pad 314 optionally includes a plurality of ribs 318 extending laterally across landing pad 314. Ribs 318 stand in relief on the posterior surface 316 of landing pad 314 to enhance engagement with the soft palate tissue, as well as help to channel the vacuum flow laterally. Ribs 318 may comprise tubular, round, or partially-round strips affixed to landing pad 314, or ribs 318 may be integrally formed with landing pad 314. Ribs may also be provided along the superior surface of plate 313 oriented either laterally like ribs 318 illustrated, in the anterior-posterior direction, or in other orientations.

A further difference from the embodiment of FIGS. 12A-D is the vacuum tube 320, which extends past apex A to a point near the posterior edge 315 of oral device 310. In this way, vacuum tube 320 ensures that negative pressure is applied along the posterior edge of oral device 310, a location closer to the soft palate. Vacuum tube 320 includes side holes 322 and an open distal end 324 through which negative pressure may be applied. Additionally, in this embodiment, tongue constraint 312 has no vacuum ports extending through plate 313 as in the earlier embodiment.

Another unique aspect of oral device 310 is the placement of spacing elements 324 on the inferior surface 326 of bite structure 311. Spacing elements 324 are a soft pliable material, e.g. polymeric tubing or foam, having a thickness of about 2-12 mm. Each spacing elements 324 is positioned at or near a posterior end 329 of bite structure 311 and extends anteriorly approximately 25-75% of the way around to the front of bite structure 311. Alternatively, multiple spacing elements of shorter length may be placed at intervals along each side of bite structure 31. In this way spacing elements 325 sit between the patient's upper and lower teeth and hold open the lower jaw slightly. Such slight opening of the jaw during sleep has been shown to improve airway patency in some circumstances.

A further unique aspect of oral device 310 is that a jaw positioning tab 328 is disposed on the anterior closed end of bite structure 311 and extends downwardly therefrom sufficiently to engage the posterior surface of the lower front teeth when oral device 310 is positioned in the oral cavity. Jaw positioning tab 328 is of sufficient stiffness and positioned in a suitable location on bite structure 311 to maintain the patient's lower jaw in a position slightly forward of a normal relaxed position. Such forward positioning of the jaw has been found to improve airway patency in some circumstances.

It should be understood that ribs 318, spacing element 324, and jaw positioning tab 328 are optional features of oral device 310 and that any or both of these features may be eliminated without departing from the scope of the invention or limiting its utility.

In other respects oral device 310 is similar to oral device 280 of FIGS. 12A-D and operates in the same way. It will be understood that oral device 310 will usually include a lip seal like lip seal 306 of the previously described embodiment although in FIGS. 13A-D the lip seal is removed for added clarity. It should be further understood that any or all of the features of oral device 310 may optionally be included in oral device 280 or in other embodiments described herein.

Figure 14A:
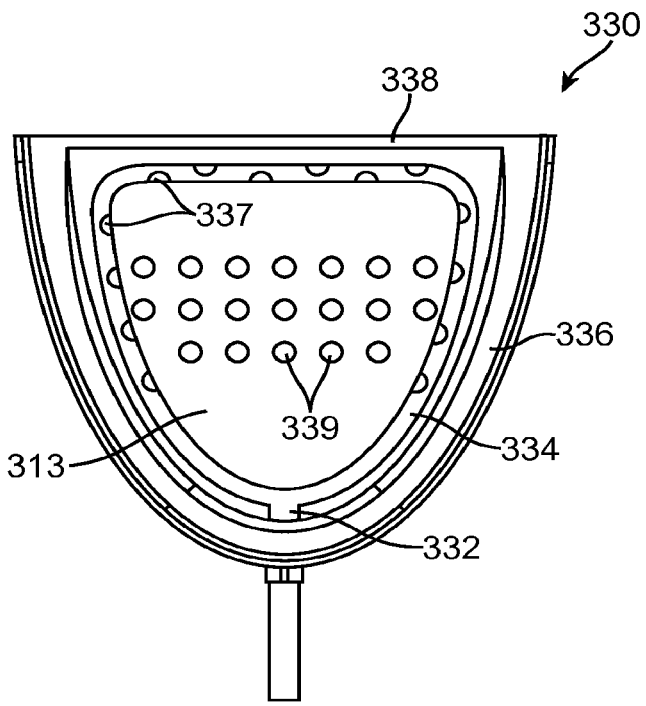
FIGS. 14A-14C are top, front and side cross-sectional views, respectively of an oral device according to the invention in still another embodiment thereof, in which the lip seal is removed for clarity.
Figure 14B:
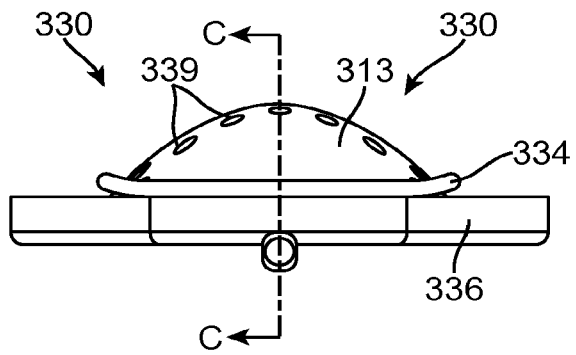
Figure 14C:
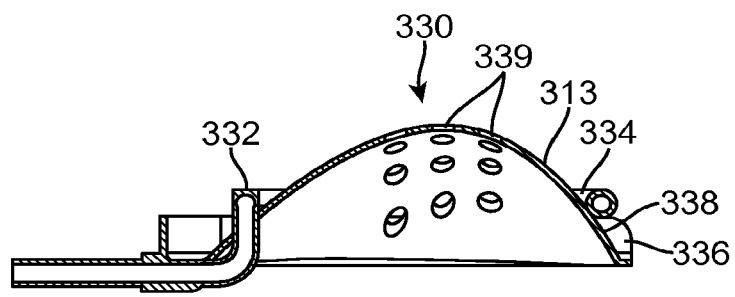

FIGS. 14A-C illustrate an oral device 330 identical to oral device 280 of FIGS. 12A-D except an alternative configuration of vacuum tube 320 is shown. In this embodiment, vacuum tube 332 has a loop 334 extending around tongue constraint 313 near the outer edges thereof adjacent bite structure 336 and along the posterior edge 338 of tongue constraint 313. Vacuum tube 320 has a plurality of side holes 337 distributed evenly around loop 334. A plurality of vacuum ports 339 are disposed in a central region of tongue constraint 313 with loop 334 encircling most if not all of vacuum ports 339. In this way negative pressure is distributed by vacuum tube 320 directly to the outer edges and posterior region of tongue constraint 313 to ensure adequate negative pressure is available in those regions. In addition, loop 334 more evenly distributes negative pressure across a larger portion of the surface of tongue constraint 313.

FIGS. 15A-D illustrate an oral device 340 according to the invention similar in many respects to oral device 280 of FIGS. 14A-D except, in place of vacuum tube 320, oral device 340 has tongue constraint 341 having a hollow interior chamber 342 enclosed between a superior wall 344 and an inferior wall 346. A vacuum tube 348 is in fluid communication with chamber 342 and extends through inferior wall 346 and anteriorly through bite structure 350 where it may be connected to a vacuum source. A plurality of inferior vacuum ports 352 extend through inferior wall 346 in communication with chamber 342 and are positioned so as to apply suction to the tongue. A plurality of posterior vacuum ports 354 extend through superior wall 344 in communication with chamber 342 and are oriented to face in a posterior direction away from the tongue and toward the soft palate. Preferably, at least some of posterior ports 354 are disposed in a plane P which is at an angle β of at least about 45°, more preferably about 60°-180°, and most preferably about 90°-180° in the superior direction relative to the occlusal plane 0 which contains the inferior surface 349 of bite structure 343. Optionally, posterior vacuum ports 354 may be further distributed along the upper portion of superior wall 344 so as to face the hard palate. In this way, vacuum may be conveyed through vacuum tube 348 into chamber 342, from which suction is applied to the tongue through inferior vacuum ports 352 and to the soft palate through posterior vacuum ports 354.

Figure 16A:
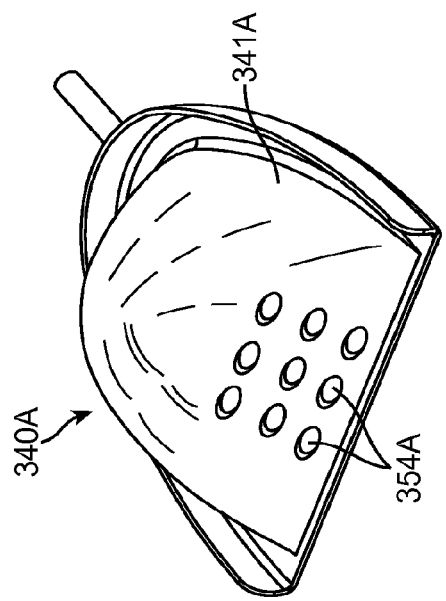
FIGS. 16A-16C are oblique, front, and side cross-sectional views, respectively of an oral device according to the invention in still another embodiment thereof, in which the lip seal is removed for clarity.
Figure 16C:
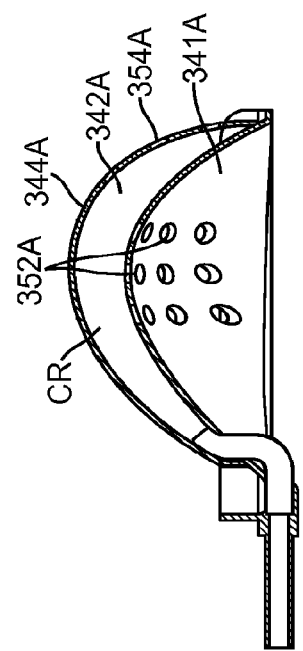
Figure 16B:
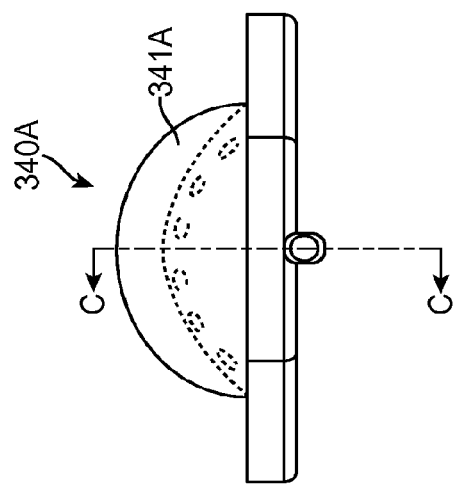

In the embodiment of FIGS. 15A-D, tongue constraint 341 has an overall thickness (or height) greater than that of oral device 280 in order to provide room for chamber 342; however, superior wall 344 will preferably be configured so that a clear region is maintained above tongue constraint 341 between the top surface of superior wall 344 and the hard palate when oral device 340 is positioned in the oral cavity. As an alternative, FIGS. 16A-C illustrate an oral device 340A substantially identical to oral device 340 except in this embodiment, the superior wall 344A extends upwardly to the hard palate such that the clear region CR formed by tongue constraint 341A is enclosed within chamber 342A. In this embodiment, superior wall 344A is shaped so as to conform generally to the shape of the hard palate and there will be little or no space between superior wall 344A and the surface of the hard palate when oral device 340A is positioned in the oral cavity. Posterior ports 354A as well as inferior ports 352A are thus in direct communication with the clear region CR within chamber 342A. As in the embodiment of FIGS. 15A-D, posterior ports 354A face away from the tongue and toward the hard palate, preferably lying in a plane which forms an angle of at least about 45°, more preferably about 60°-180°, and most preferably about 90°-180° in the superior direction relative to the occlusal plane.

In the embodiment of FIGS. 17A-D, oral device 360 is similar to oral device 340 of FIGS. 15A-D, except that tongue constraint 362 comprises two separate hollow chambers within it, including an anterior chamber 364 and a posterior chamber 366, each enclosed by a superior wall 368 and an inferior wall 370. Preferably, tongue constraint 362 is a molded construction with anterior chamber 364 and posterior chamber 366 integrally formed within it. A transverse wall 372 divides anterior chamber 364 from posterior chamber 366. A plurality of inferior ports 374 are disposed in inferior wall 370 in communication with anterior chamber 364, and a plurality of posterior ports 376 are disposed in superior wall 368 in communication with posterior chamber 366. As in other embodiments, inferior ports 374 are positioned so as to apply suction to the tongue, while posterior ports 376 are positioned so as to face away from the tongue and toward the soft palate in order to apply suction to the soft palate and not be blocked by the tongue when it is engaged by inferior wall 370. As described above in connection with FIGS. 15A-D, at least some of posterior ports 376 are disposed in a plane which is at an angle of at least about 45°, more preferably about 60°-180°, and most preferably about 90°-180° in the superior direction relative to the occlusal plane. An anterior supply conduit 380 extends through tongue constraint 362 from anterior chamber 364 to the anterior end of tongue constraint 362, while a posterior supply conduit 382 extends from posterior chamber 366 to the anterior end of tongue constraint 362. A first vacuum tube 384 connects to anterior supply conduit 380 and a second vacuum tube 386 connects to posterior supply conduit 382, each vacuum tube extending through bite structure 388 and being configured to connect to a vacuum source.

Figure 17A:
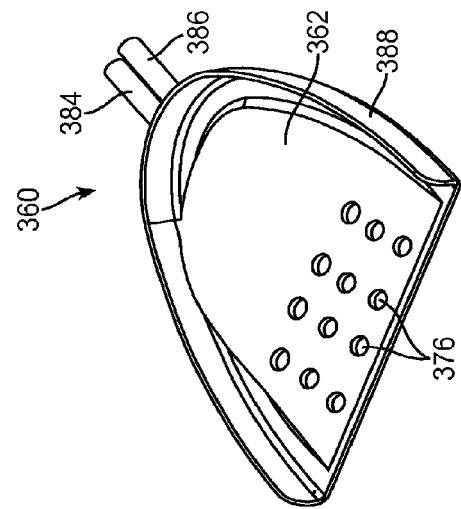
FIGS. 17A-17D are top cutaway, oblique, front and side cross-sectional views, respectively of an oral device according to the invention in still another embodiment thereof, in which the lip seal is removed for clarity.
Figure 17B:
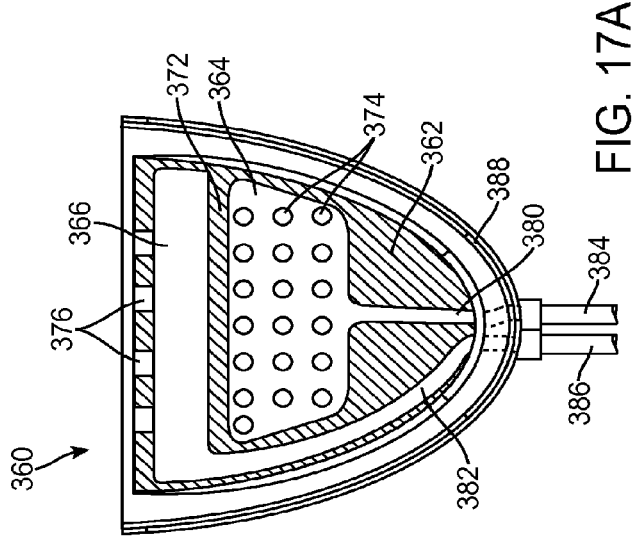
Figure 17C:
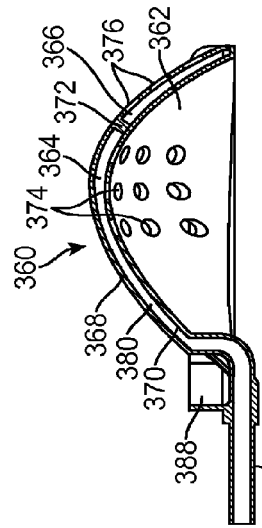
Figure 17D:
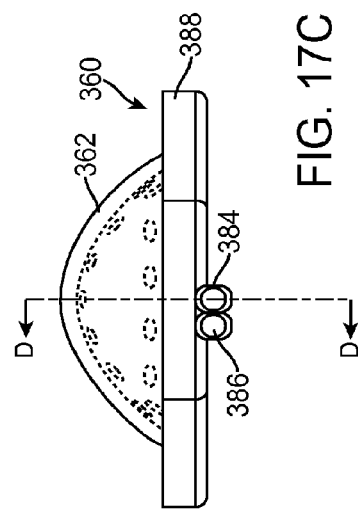
Figure 17E:
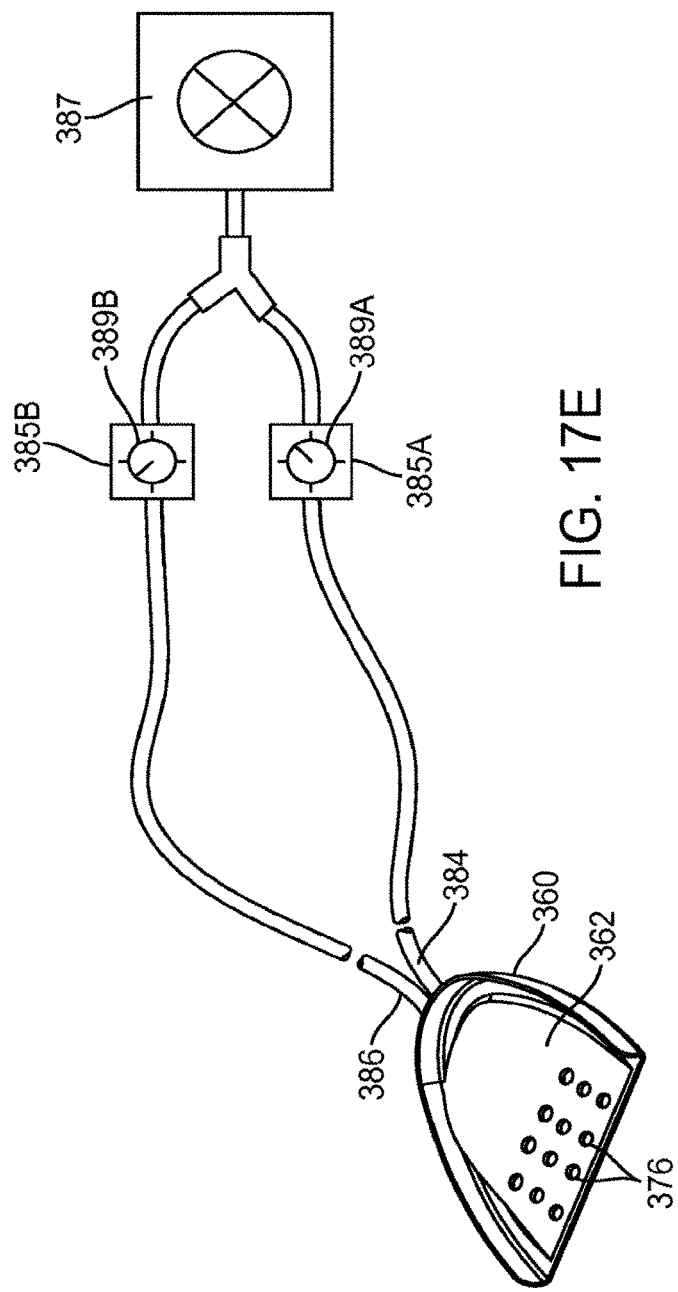
FIG. 17E is a schematic illustration of a system for applying different pressures to different regions of the oral cavity shown with the oral device of FIGS. 17A-D.

Oral device 360 is particularly advantageous in that the negative pressures within anterior chamber 364 and posterior chamber 366 can be controlled independently of one another. As illustrated in FIG. 17E, vacuum tubes 384, 386 may be connected to separate pressure regulators 385A, 385B, which are in turn fluidly connected to a single vacuum pump 387. Pressure regulators 385 are adjustable using control knobs 389A, 389B to set the level of negative pressure applied through each of vacuum tubes 384, 386. In this way, the negative pressure in each of anterior chamber 364 and posterior chamber 366 (not shown in FIG. 17E) can be independently controlled and optimized to keep the soft palate and tongue free of the airway. For example, different pressures could be applied to different regions of the oral cavity (e.g. the tongue and the soft palate) to achieve the desired displacement of different tissues. In addition, air under positive pressure can be delivered through either vacuum tube 384 or vacuum tube 386 while air at a different pressure or negative pressure is delivered through the other vacuum tube, for purposes of removing saliva from the vacuum tubes, delivering positive pressure to the airway or other regions, or achieving other desired effects. In an alternative embodiment, vacuum tubes 384, 386 may be connected to two separate pumps which are independently controllable to adjust the level of positive or negative pressure delivered, as shown in FIG. 21C, described below.

Figure 18C:
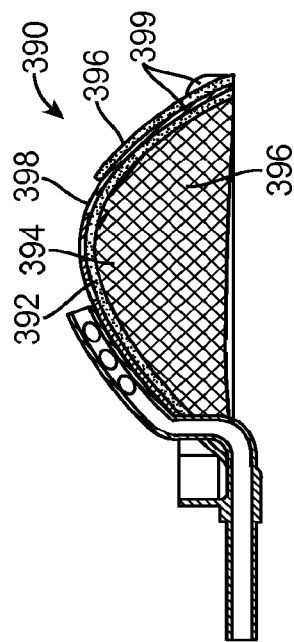
FIGS. 18A-18C are top, oblique and side cross-sectional views, respectively of an oral device according to the invention in still another embodiment thereof, in which the lip seal is removed for clarity.
Figure 18B:
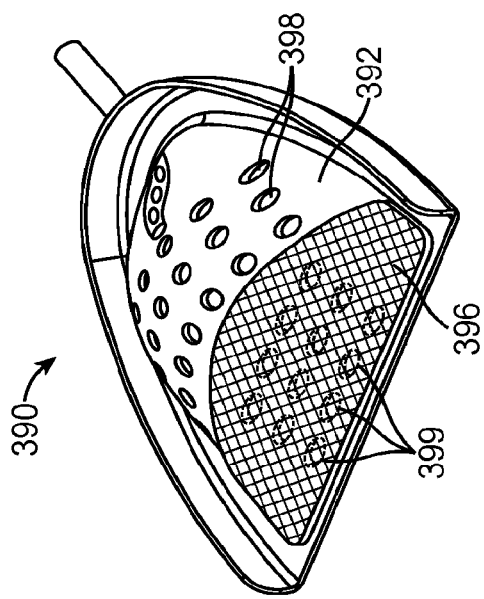
Figure 18A:
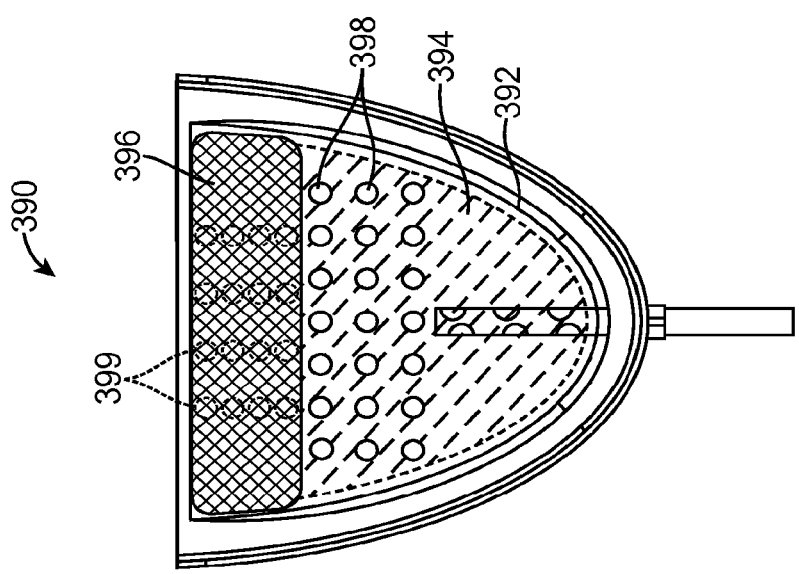

Turning to FIGS. 18A-C, in a further embodiment, oral device 390 is constructed identically to oral device 280 of FIGS. 12A-D except that tongue constraint 392 includes an inferior pad 394 adhered to the inferior surface of tongue constraint 392, and a posterior pad 396 adhered to a posterior surface of tongue constraint 392. Inferior pad 394 and posterior pad 396 are composed of a soft, flexible and porous material such as Dacron, cotton, or foam, and are adapted to reduce friction and abrasion of the tongue and/or soft palate tissues which engage tongue constraint 392. Inferior pad 394 and posterior pad 394 are sufficiently porous to allow vacuum to be applied through them from inferior vacuum ports 398 or posterior vacuum ports 399. It should be appreciated that either inferior pad 394 or posterior pad 396 may optionally be used without the other, and that either or both inferior pad 394 or posterior pad 396 could be used with any of the other embodiments described above or below.

Figure 19A:
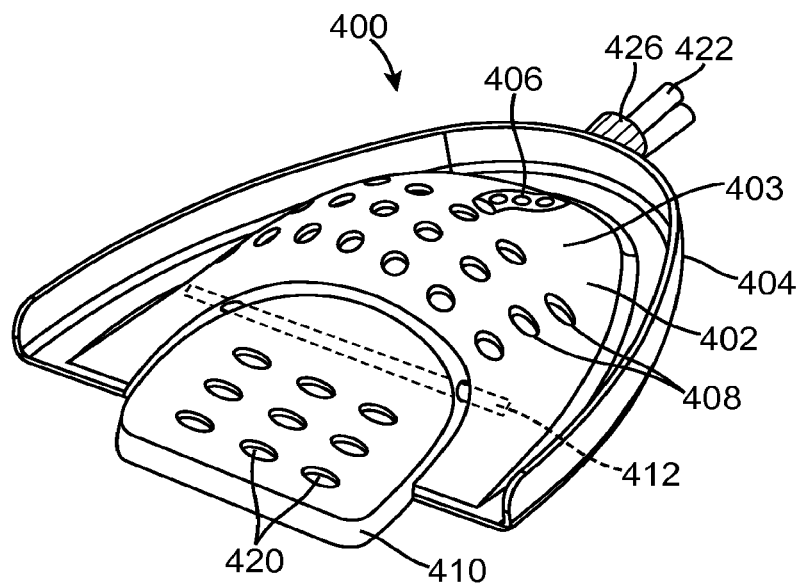
FIGS. 19A-19B are oblique and side cross-sectional views, respectively of an oral device according to the invention in still another embodiment thereof, in which the lip seal is removed for clarity.
Figure 19B:
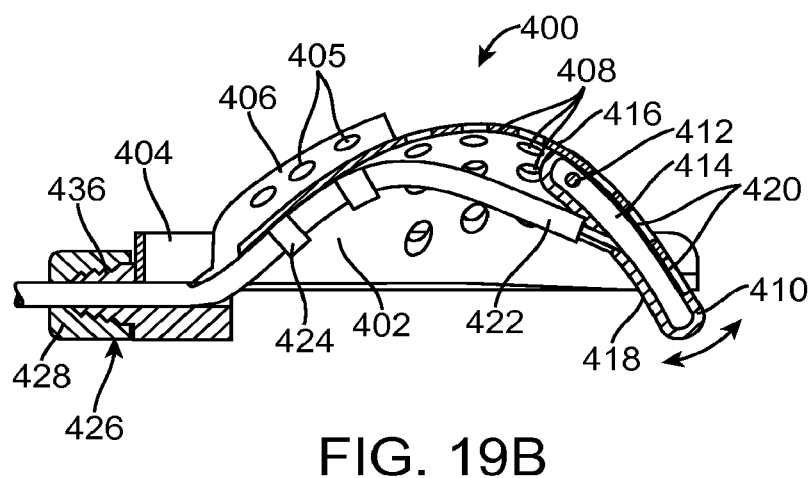

FIGS. 19A-B illustrate a further embodiment of an oral device according to the invention. In this embodiment, like other embodiments elsewhere described, oral device 400 comprises a tongue constraint 402 and a bite structure 404. Tongue constraint 402 comprises a dome-shape plate 403 with a plurality of inferior vacuum ports 408 extending through plate 403 in a central region thereof. An anterior vacuum tube 406 is fixed to the superior surface of plate 403 and has a plurality of side holes 405 through which vacuum may be conveyed.

Different from previously describe embodiments, a landing pad 410 is pivotally coupled to tongue constraint 402 by a transverse pin 412, so that landing pad 410 is rotationally movable relative to plate 403. Landing pad 410 has a hollow interior chamber 414 enclosed by a posterior wall 416 and an anterior wall 418. A plurality of posterior ports 420 are disposed in posterior wall 416 in communication with chamber 414. As in the embodiments of FIGS. 15-17, posterior ports 420 are configured to face the soft palate and away from the tongue, preferably being disposed plane which is at an angle β of at least about 45°, more preferably about 60° 180°, and most preferably about 90°-180° in the superior direction relative to the occlusal plane. Notably, the angle of posterior ports 420 relative to the occlusal plane may be varied by pivoting landing pad 410 relative to plate 403.

A posterior vacuum tube 422 is connected to anterior wall 418 in communication with chamber 414. Posterior vacuum tube 422 extends anteriorly along the inferior side of plate 403, which optionally may include eyelets 424 through which posterior vacuum tube is slidably positioned to keep it close to plate 403. Posterior vacuum tube 422 extends slidably through bite structure 404 and a clamp 426 fixed to the anterior side thereof. Clamp 426 has a cap 428 threaded onto a tapered receptacle 430 each having a central passage through which posterior vacuum tube extends. Tapered receptacle 430 may be axially split and/or sufficiently conformable that tapered receptacle 430 is urged radially inward to engage posterior vacuum tube 422 as cap 428 is rotationally tightened. Of course, various clamps suitable for clamping posterior vacuum tube 422 are well known and may be used in place of the exemplary clamp illustrated. By sliding posterior vacuum tube 422 anteriorly or posteriorly, landing pad 410 is pivoted relative to plate 403. It should be understood that pull wires, rods, or other means could be used instead of posterior vacuum tube to pivot landing pad 403.

Advantageously, different negative pressures may be applied through anterior vacuum tube 406 and posterior vacuum tube 422 so that the suction applied to the soft palate through posterior ports 420 may be controlled independently of the suction applied to the tongue through inferior ports 408. For example, oral device 400 may be used with the system illustrated in FIG. 19E or the system illustrated in FIG. 23C. When vacuum has been applied through posterior ports 420 such the soft palate has become engaged against landing pad 410, posterior vacuum tube 422 maybe tensioned to pivot landing pad 410 anteriorly, thereby helping to draw the soft palate further away from the patient's airway. Once landing pad 410 is in the desired position, clamp 426 may be tightened to lock the posterior vacuum tube 422 and landing pad 410 in place.

Referring now to FIGS. 20 and 20A-B, in a further embodiment an oral device 434 comprises a tongue constraint 436 movably coupled to a bite structure 438. Tongue constraint 436 has a superior wall 440 and an inferior wall 442 enclosing a hollow chamber 444. A plurality of inferior ports 446 extend through inferior wall 442 in communication with chamber 444. A plurality of posterior ports 448 are disposed in a posterior region of superior wall 440 in communication with chamber 444. Posterior ports face toward the soft palate and away from the tongue to remain unobstructed by the tongue when vacuum is applied therethrough, preferably lying in a plane which is at an angle of at least about 45°, more preferably about 60°-180°, and most preferably about 90°-180° in the superior direction relative to the occlusal plane. A vacuum tube 450 is connected to tongue constraint 436 in communication with chamber 444 and extends slidably through a channel 452 in bite structure 438. A clamp 454 is mounted to bite structure 438 and is adapted to lock vacuum tube 450 in position relative to bite structure 438. Clamp 454 may be constructed like clamp 426 of FIGS. 19A-B or may have any other known clamp design suited for its purpose.

Bite structure 438 is U-shaped with a closed anterior end 439, an open posterior end 441, and an inner wall 456 along its interior side. A pair of channels 458 are disposed in inner wall 456 on opposing sides of bite structure 438 near its open end 441. A pair of pins 460 are attached to opposing lateral sides of tongue constraint 436 and extend laterally through channels 458. Pins 460 are slidable in channels 458 so that tongue constraint 436 is movably anteriorly and posteriorly relative to bite structure 438. In this way, vacuum may be applied through vacuum tube 450 and chamber 444 so as to apply suction through inferior ports 446 to the tongue, and through posterior ports 448 to the soft palate. When these tissues have been engaged, tension may be exerted on vacuum tube 450 to move tongue constraint 436 anteriorly relative to bite structure 438, thereby retracting the tongue and soft palate further forward and away from the airway. Once in the desired position, vacuum tube 450 may be clamped in place by tightening clamp 454 so as to hold tongue restraint 436 in position relative to bite structure 438.

Figure 21A:
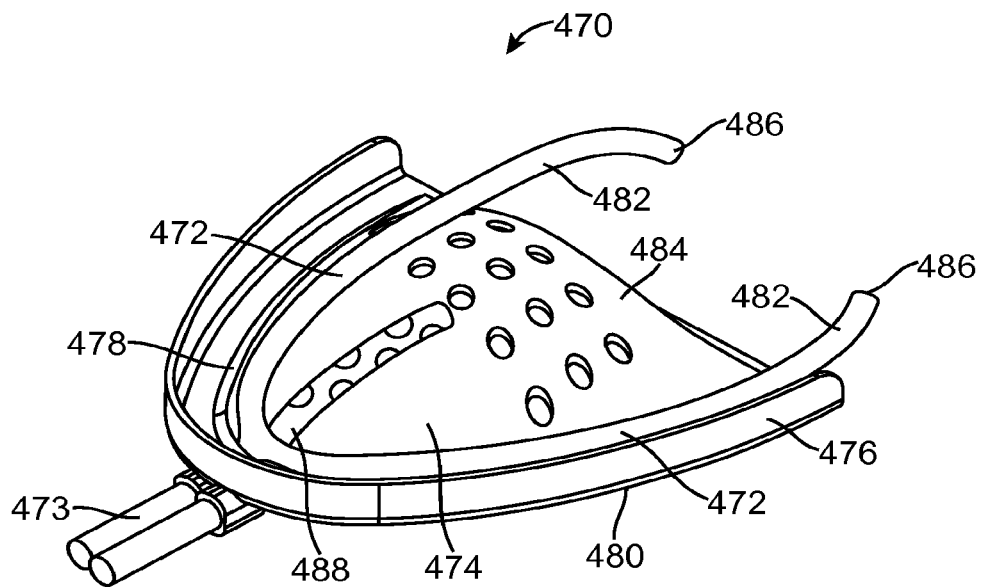
FIGS. 21A-21B are oblique and side cross-sectional views, respectively of an oral device according to the invention in still another embodiment thereof, in which the lip seal is removed for clarity.
Figure 21B:
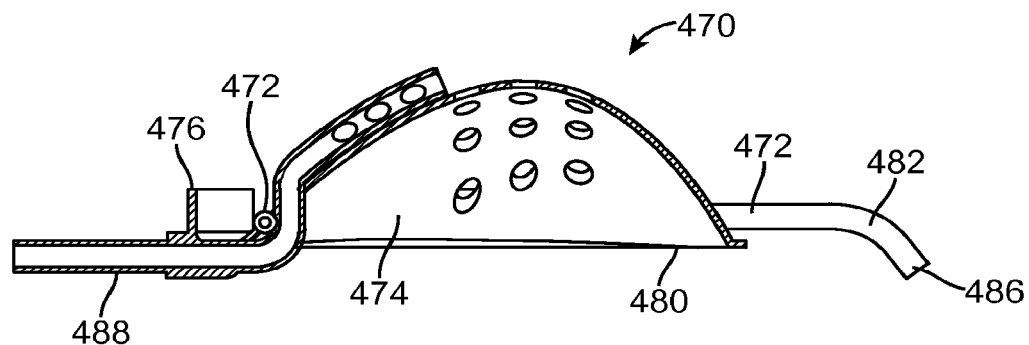
Figure 21C:
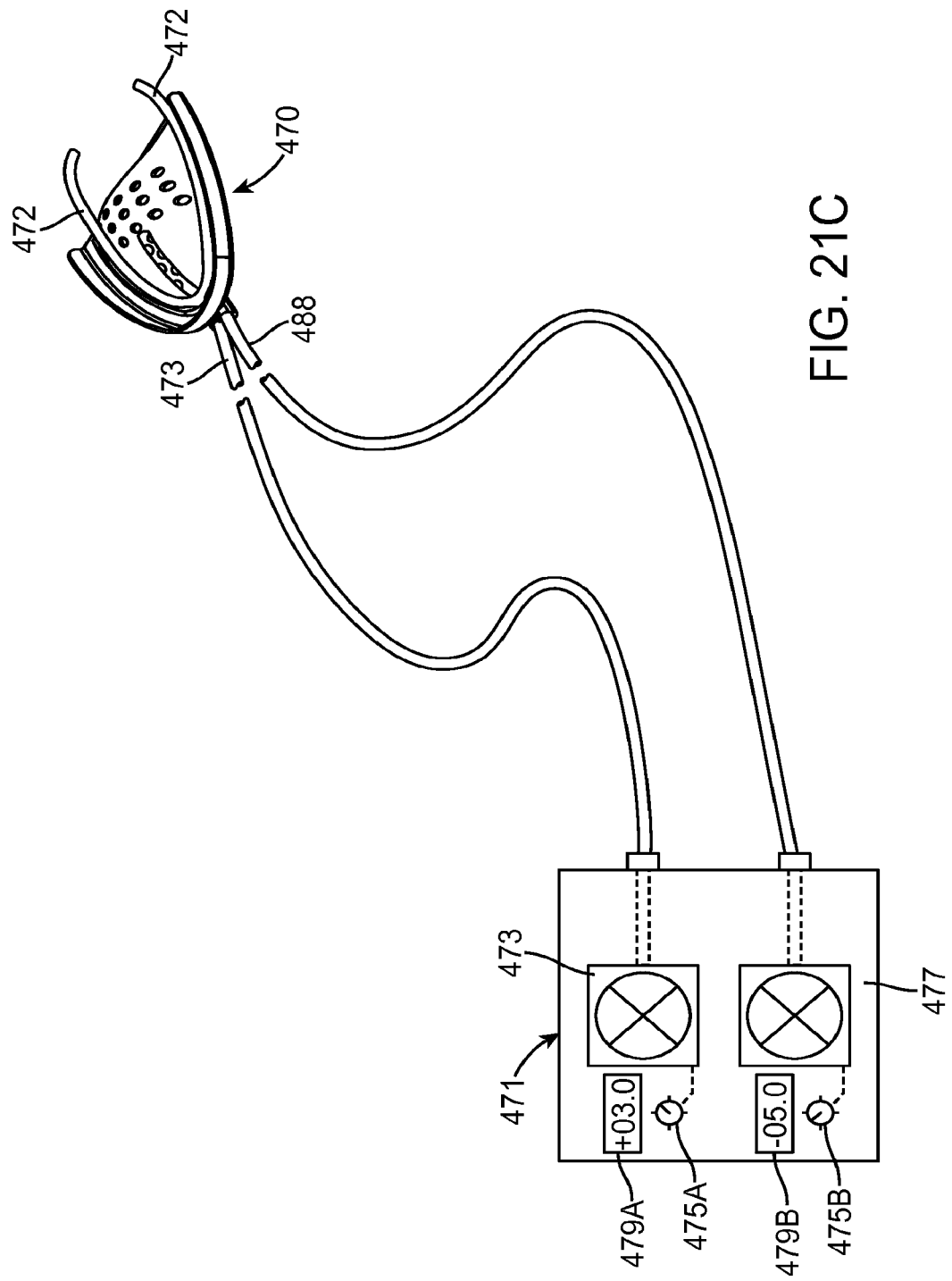
FIG. 21C is a schematic illustration of a system for delivering different pressures to different regions of the oral cavity, shown with the oral device of FIGS. 23A-B.

FIGS. 21A-B illustrate another embodiment of an oral device according to the invention. In this embodiment, oral device 470 is identical to oral device 280 of FIGS. 12A-D except that oral device 470 is adapted to deliver air under positive pressure into the patient's airway while the tongue is constrained and negative pressure is applied to the soft palate and tongue. Oral device 470 includes at least one, preferably two (as shown), delivery conduits 472 fixed to the upper surface of tongue constraint 474. Alternatively delivery conduits 472 may be fixed to bite structure 476, e.g. to its inner wall 478 or to its inferior surface 480. In the latter case delivery conduits 472 may serve the additional purpose of acting as a spacer between the patient's upper and lower teeth to keep them slightly apart when the oral device is in place. As a further alternative, all or part of delivery conduits 472 may be formed by an interior lumen (not shown) formed integrally within tongue constraint 474 or bite structure 476. Delivery conduits 472 have posterior portions 482 extending from the posterior edge 484 of tongue constraint 474 with free posterior ends 486 adapted to extend into the patient's airway. Delivery conduits 472 connect to a delivery tube 473 which extends through bite structure 476 and is adapted to connect to a fluid supply tube (not shown) outside the patient's oral cavity, which in turn may be connected to pump (not shown) for delivering air or other gasses under positive pressure. Alternatively, delivery tube 473 may be open to room air so that the airway is in communication with air outside the oral cavity in order to allow mouth breathing while the device is in place and while the oral cavity seal is maintained.

As in the case of oral device 280, with oral device 470 in place in the patient's oral cavity, tongue constraint 474 maintains at least a portion of the tongue in a position spaced apart from the patient's hard palate so as to maintain a clear region superior to tongue constraint 474. Negative pressure may be applied through vacuum lumen 488 to exert vacuum force on the soft palate and tongue, thereby causing the soft palate and tongue to be maintained in sealing engagement with one another anterior to the patient's airway, isolating the airway from the remainder of the oral cavity. The soft palate, tongue, and oral device may alternatively seal to each other in any combination in order to substantially fluidly isolate the airway. In this embodiment, delivery conduits 472 are adapted to extend into the airway between the soft palate and tongue while still allowing these tissues to seal against each other and around the periphery of delivery conduits 472. Air or other suitable gasses may be delivered to the airway under positive pressure through delivery conduits 472 thereby enhancing the pressure gradient between the airway and the oral cavity, helping to urge the soft palate and tongue anteriorly out of the airway and preferably in sealing engagement with one another. Positive pressure delivered to the airway may also apply forces to other tissues in a manner that improves airway patency.

A dual-pump system for use with oral device 470 is illustrated in FIG. 21C. System 471 comprises a first pump 473 controlled via a control knob 475A and a second pump 477 controlled via a second control know 475B. A first readout 479A displays the pressure level being applied by first pump 473, while a second readout 479B displays the pressure level being applied by second pump 477. Delivery tube 473 is connected to first pump 473 while vacuum tube 488 is connected to second pump 477. In this way, first pump 473 may deliver air under an adjustable level of positive pressure through delivery conduits 472, while second pump 477 may be adjusted to apply a desired level of negative pressure through vacuum lumen 488. Optionally, pressure lumens or sensors may be provided on oral device 470 to monitor negative pressure in the oral cavity and/or positive pressure in the airway. These may be coupled to first and second pumps 473, 477 which may be automatically controlled to adjust pump speed or pressure to maintain desired pressure levels or a desired pressure gradient between the airway and the oral cavity.

Figure 22A:
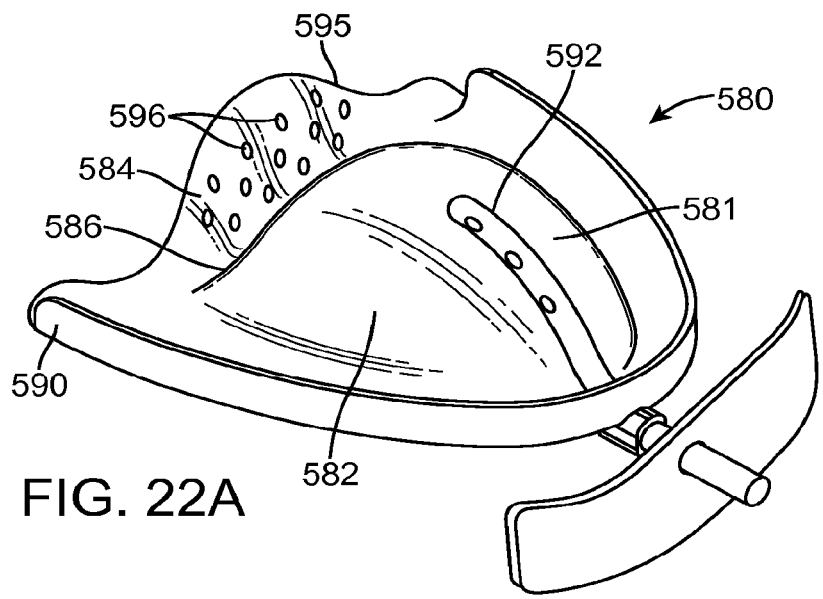
FIGS. 22A-22C are oblique, top, and side cross-sectional views, respectively of an oral device according to the invention in still another embodiment thereof.
Figure 22B:
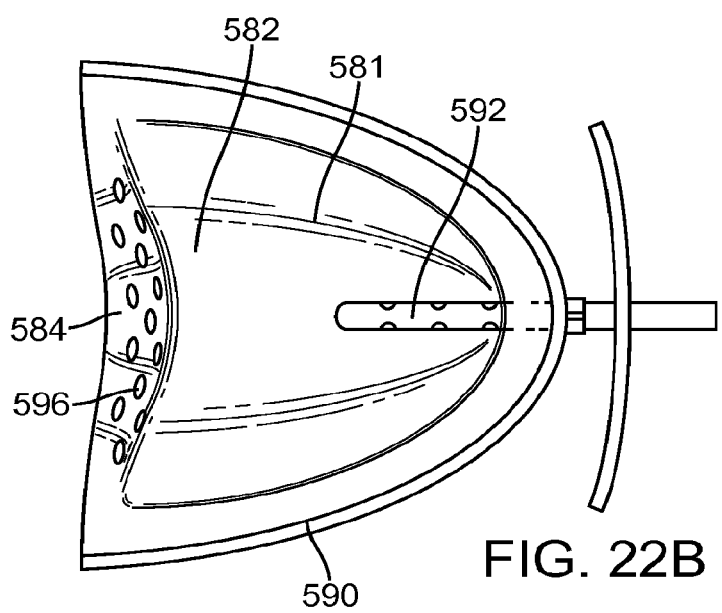
Figure 22C:
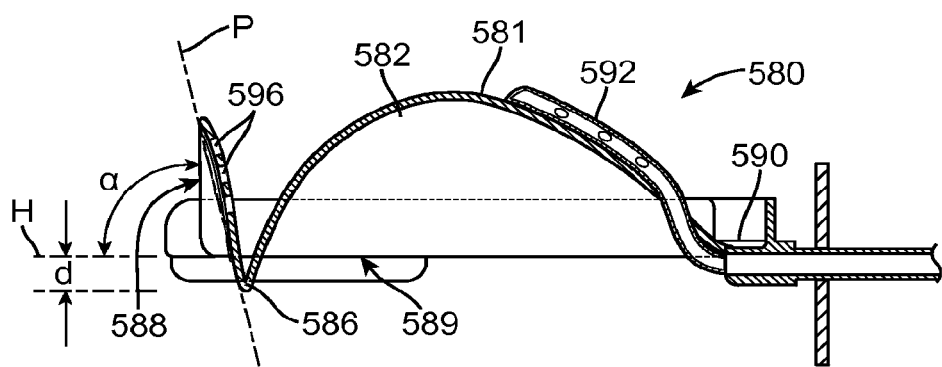

In a further embodiment of the invention, illustrated in FIGS. 22A-C, an oral device 580 is substantially identical to oral device 280 of FIGS. 12A-D, except in this embodiment, oral device 580 comprises a tongue constraint 581 having a plate 582 for engaging the patient's tongue and a landing pad 584 which extends in a generally superior direction from a posterior edge 586 of plate 582. As shown in FIG. 22C, landing pad 584 has a posterior surface 588 at least a portion of which lies in a plane P which is at an angle a of at least about 30°, more preferably about 45-135°, and most preferably about 60-100° relative to the occlusal plane H containing the inferior surface 589 of bite structure 590. In this way, posterior surface 588 is configured to receive and engage the soft palate as it is drawn forward by vacuum pressure applied through vacuum tube 592. Posterior surface 588 may have a curvature either or both laterally right-left and superiorly-inferiorly so as to present a concave surface into which the soft palate is drawn. The superior edge 595 of landing pad 584 preferably has an arched shape corresponding to the shape of the hard palate, and may be configured to engage the hard palate and even to seal therewith, or alternatively may be spaced apart from the hard palate. In addition, posterior edge 586 of plate 582, which forms the inferior edge of landing pad 584, may be disposed in various positions relative to the occlusal plane H, including both superior and inferior to plane H. In a particular embodiment, posterior edge 586 is disposed a distance d of about 2-7 mm, more preferably about 3-6 mm, inferior to plane H.

A plurality of posterior ports 596 are disposed in landing pad 584 and extend through its thickness so that, with oral device 580 in place in the patient's oral cavity, posterior ports 596, lying in plane P, face in a posterior direction directly toward the soft palate. In this way, the clear region created superior to plate P and below the hard palate communicates directly with the soft palate through posterior ports 596 so that vacuum applied through vacuum tube 592 is applied directly to the soft palate via posterior ports 596. Moreover, the vertical orientation of landing pad 584 and posterior ports 596 therein allows vacuum to be applied to the entire soft palate, from its free inferior tip to its posterior end where it attaches to the hard palate, enhancing the effectiveness of displacing the soft palate from the patient's airway. Because the patient's tongue is constrained under the inferior surface of plate 582, the tongue cannot be pulled by the vacuum forces to obstruct posterior ports 596. Inferior ports (not shown) may optionally be provided in plate 582 through which vacuum may be exerted upon the superior surface of the tongue, similar to the embodiment of FIGS. 12A-D.

Figure 23A:
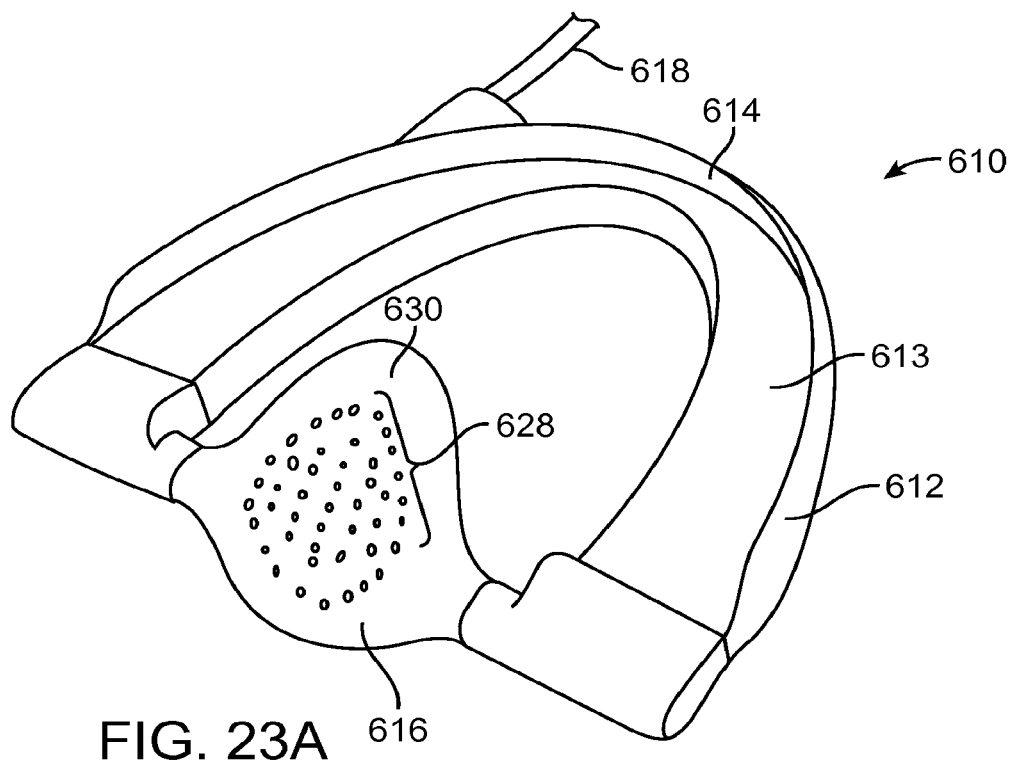
FIGS. 23A and 23B illustrate a further embodiment of an oral device constructed in accordance with the principles of the present invention, with FIG. 23A shown in full line perspective view and FIG. 23B shown with portions broken away.
Figure 23B:
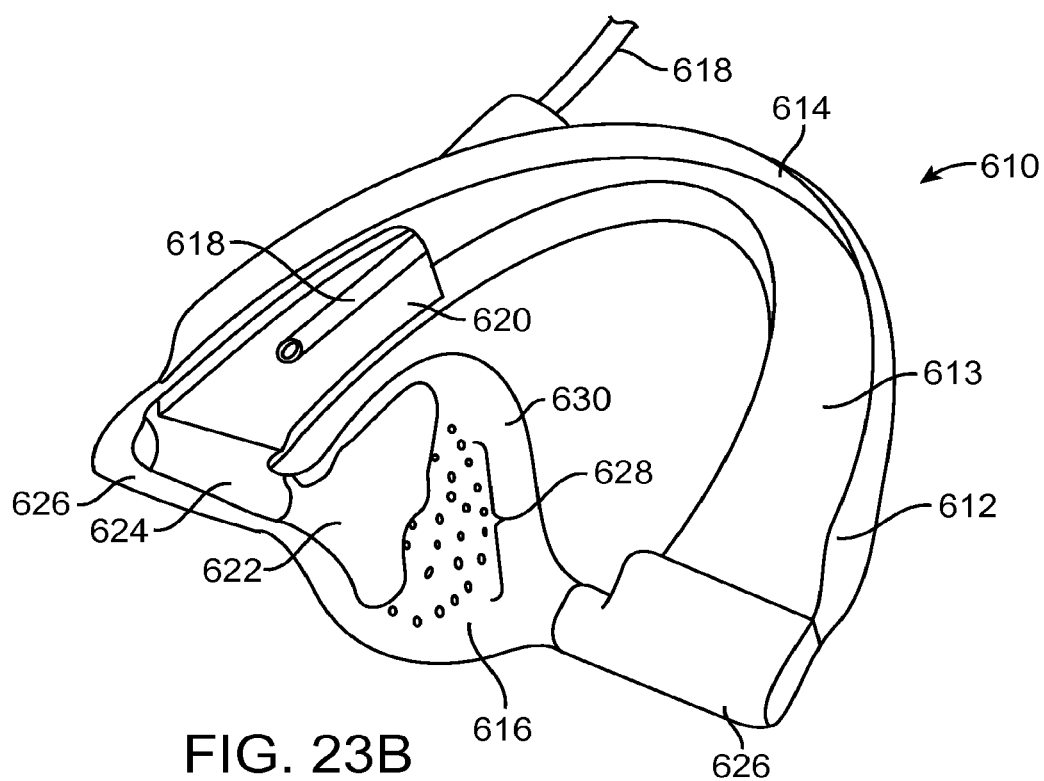

Referring now to FIGS. 23A and 23B, a further exemplary oral device 610 constructed in accordance with the principles of the present invention comprises a U-shaped base or anchor structure 612 having a lip seal 614 at its forward or anterior end. A tongue-engaging member 616 is held between the posterior ends of right and left legs of the U-shaped base 612, and a vacuum tube 618 passes into the device and is open within a plenum 620 in order to draw a vacuum within the device. In particular, the plenum 620 is open to an interior 622 of the tongue-engaging member 616 so that the vacuum may be drawn via a conduit 624 provided through one of the connecting wings 626 which couple the tongue-engaging member 616 to the base 612. A plurality of ports 628 are formed over a posterior surface 630 of the tongue-engaging member 616 so that a vacuum may be applied within the oral cavity when the device 610 is held with the base anchor 612 positioned between the patient's upper and lower teeth. Typically, the patient's teeth will be placed within upper and lower channels 613 (with only the upper channel being shown in FIGS. 23A and 23B) which are formed in the upper or superior and lower or inferior surface of the base 612.

Figure 24:
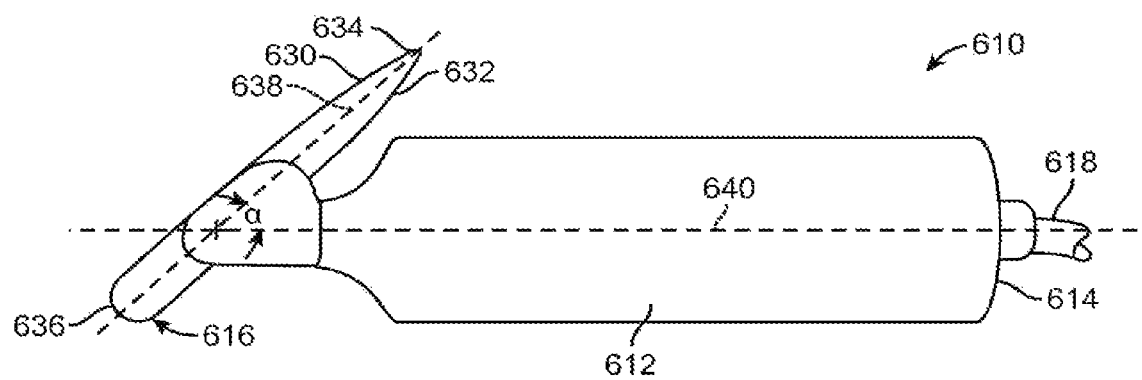
FIG. 24 is a side view of the oral device of FIGS. 23A and 23B.

As best shown in FIG. 24, the tongue-engaging member 616 has both the posterior surface 630 and an anterior surface 632, where the anterior surface will engage the tongue when the base 612 is held between the patient's teeth. The anterior surface of the tongue-engaging member will typically be flat or slightly curved in order to engage a medial region of the tongue over a relatively large surface area, typically in the range from 300 mm2 to 1000 mm2, usually from 550 mm2 to 750 mm2. Of particular interest to the present invention, the tongue-engaging member 616 will be inclined with an upper end or lip 634 displaced in an anterior direction (toward the lip seal 614) and a lower or inferior lip or edge 636 being displaced in a posterior direction. The tongue-engaging member 616 will typically have a center line 638 (shown in broken line) which is inclined at an angle a in the range from 30° to 70°, usually from 45° to 60°, relative to a plane 640 (shown in broken line) of the base, which is positioned between the patient's teeth during use of the device. The relatively large area of the anterior surface 632 of the device 610 combined with the angle of inclination, which is generally inclined forwardly relative to a plane of the base when the base is positioned between the upper and lower teeth, combines for particularly effective anterior displacement of the patient's tongue while creating a clear region above the medial region of the tongue in order to apply a vacuum to close the soft palate against the posterior region of the tongue, as described in more detail below.

Figure 25:
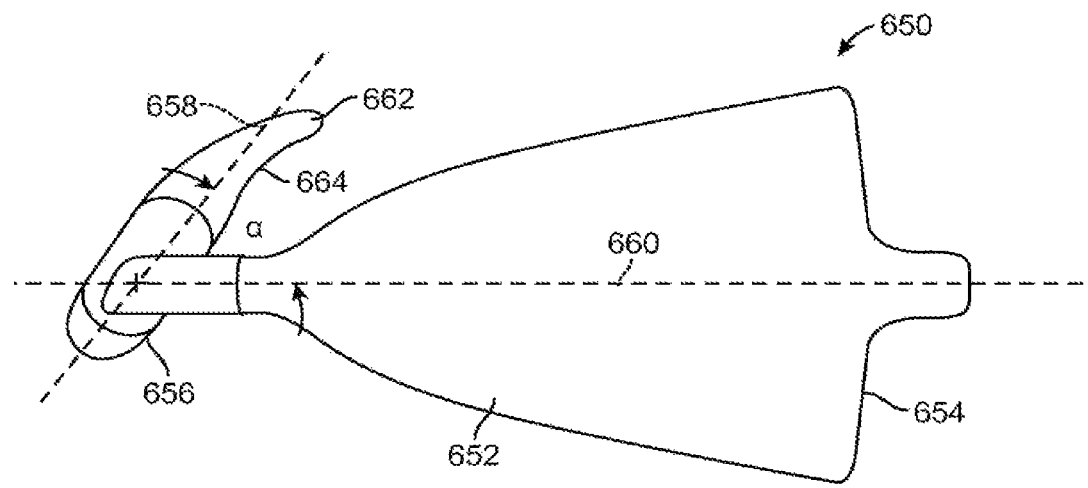
FIG. 25 is a side view of a second embodiment of a further oral device which is a variation of the device FIGS. 23A, 23B and 24.

Oral device 650 (FIG. 25) represents a second embodiment of the present invention and includes a U-shaped base or anchor 652 having an enlarged lip seal 654 at its anterior end. A tongue-engaging member 656 is carried at the posterior end of the base 652 and has a body which is generally aligned along a plane 658 (shown in broken line) which is disposed at the same angle a relative to the plane of the base 660 (broken line) as with the first device illustrated in FIG. 24. A principal difference of the oral device 650 is that an upper edge 662 of the tongue-engaging member 656 is inclined in a forward or anterior direction, generally with a curved anterior surface 664. The remaining aspects of the oral device 650 are generally the same as described above with respect to the first oral device 610. Use of the oral device 650 is described in more detail in connection with FIGS. 28 and 29.

Figure 26:
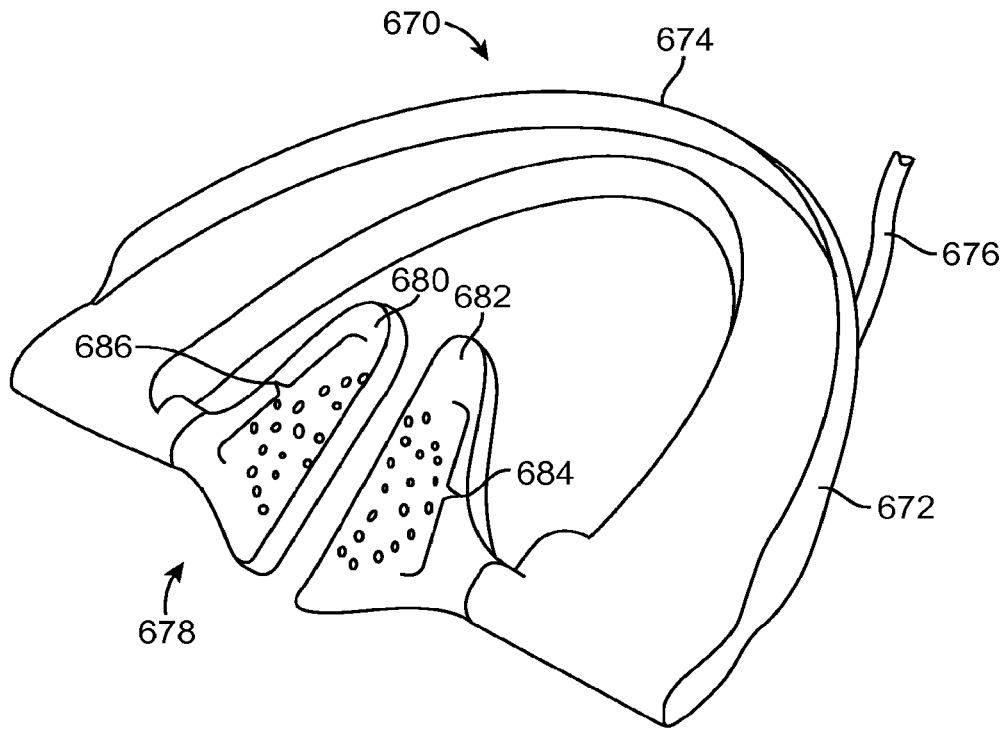
FIG. 26 is a perspective view of yet another embodiment of an oral device constructed in accordance with the principles of the present invention.

Referring now to FIG. 26, an oral device 670 comprises a U-shaped base or anchor 672 having a lip seal 674 at its forward or anterior end. A vacuum tube or line 676 is connected to the device in order to apply a vacuum within an interior of the base 672. A tongue-engaging member 678 comprises a right half 80 and a left half 682 (where right and left are viewed from the anterior end of the device which includes the lip seal 674). Each of the right and left halves 680 and 682 are connected to a vacuum plenum (not illustrated) formed through both sides of the interior of base or anchor 672 so that the vacuum applied through vacuum tube 676 is carried through to the ports 684 and 686 formed on the two halves, respectively. The angle of inclination of the two halves will typically be identical, but it could vary by a small amount without departing from the effectiveness of the present invention. The inclination angle(s) and total contact area of the anterior surfaces of the halves 680 and 682 are also within the ranges set forth above, so that the effectiveness of the device is generally the same as described for the previous devices.

Figure 27:
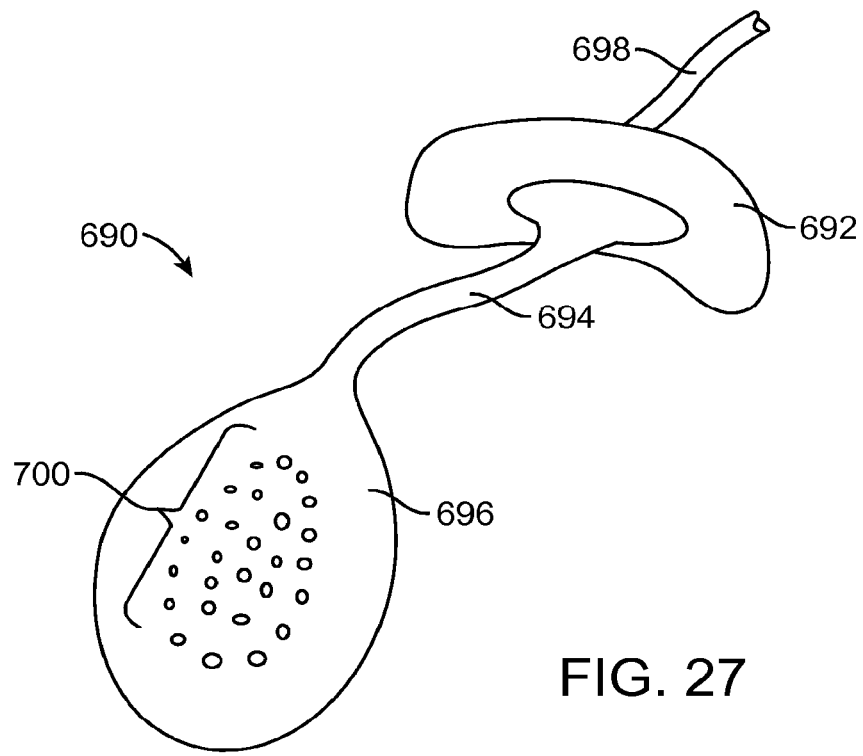
FIG. 27 is a perspective view of still another oral device constructed in accordance with the principles of the present invention.

Referring now to FIG. 27, an oral device 690 represents a fourth embodiment of the present invention and comprises an interior bite plate and lip seal 692 connected to a single axial bridge 694 which carries a tongue-engaging member 696 at its posterior end. The tongue-engaging member 696 has generally the same dimensions and is inclined at the same angle relative to a bite plane as described with the prior embodiments. A vacuum is applied through a vacuum tube 698 which is connected via a plenum (not shown) within the single axial member 694 which opens to the interior of the tongue-engaging member 696. The vacuum is applied through a plurality of ports 700. The device 690 is less bulky than the prior embodiments.

Figure 28:
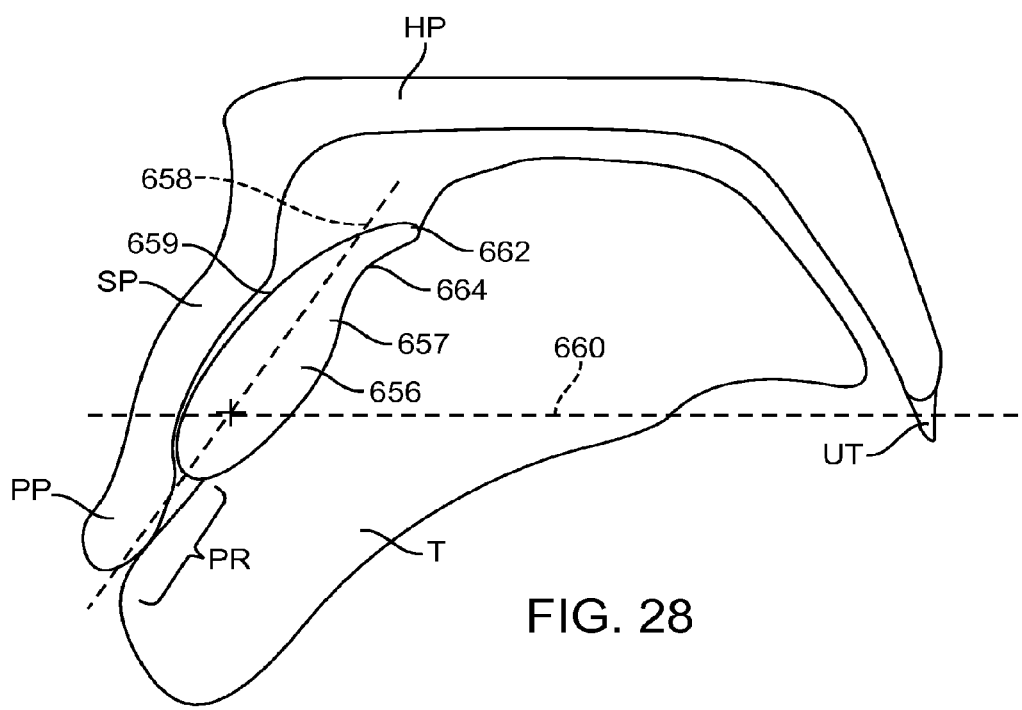
FIGS. 28 and 29 are schematic illustrations of the placement of the oral device of FIG. 25 in an oral cavity with the soft palate engaging a posterior surface of the device in FIG. 28 and the soft palate spaced-apart from the oral device in FIG. 29, but in both cases this soft palate engages a posterior portion of the tongue.
Figure 29:
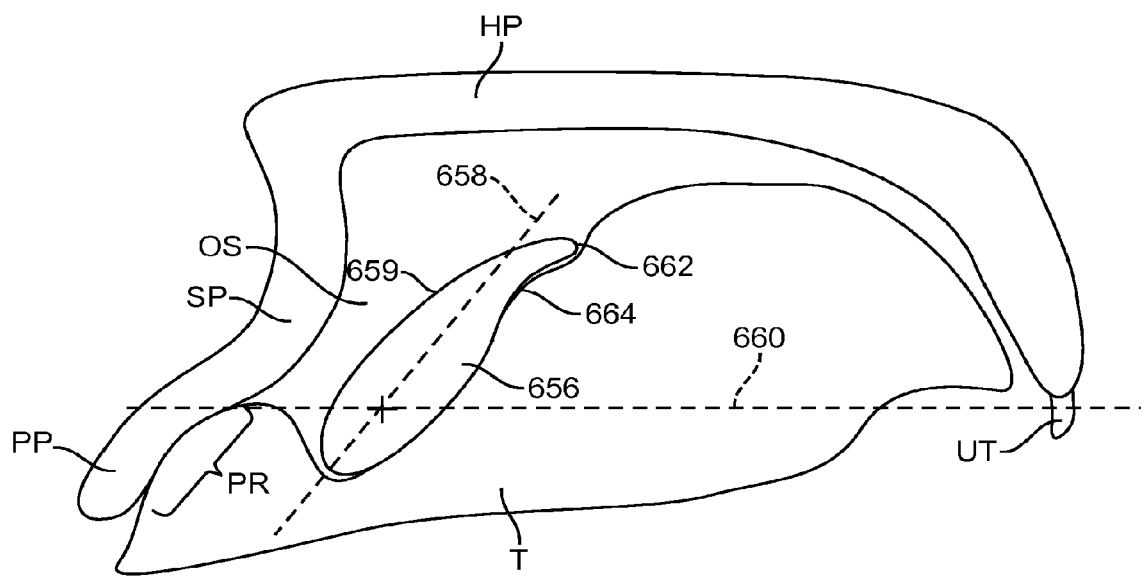

Referring to FIGS. 28 and 29, use of the device 650 for positioning tongue-engaging member 656 against a tongue within an oral cavity will be described. In a first instance, as shown in FIG. 28, anterior surface 657 of the tongue-engaging member 656 engages the medial region of the tongue T to push or displace the tongue in an anterior direction. By applying a vacuum through ports on the posterior surface 659, the soft palate SP is also drawn in an anterior direction so that a posterior portion PP of the palate seals against a posterior region PR of the tongue, as illustrated. The region of the soft palate above the posterior portion is also drawn against the posterior surface 659 of the tongue-engaging member 656, to further stabilize the soft palate to treat the breathing disorder.

The portion of the soft palate SP above the posterior portion PP need not be engaged against the posterior surface 659 of the tongue-engaging member 656. As shown in FIG. 29, an open space OS may remain between the posterior surface 659 and the soft palate SP while the posterior portion PP of the soft palate remains engaged with the posterior region PR of the tongue. The soft palate remains sufficiently stabilized in order to treat the breathing disorders within the methods of the present invention.

While the above is a complete description of the preferred embodiments of the invention, various alternatives, modifications, substitutions, and equivalents may be used. Therefore, the above description should not be taken as limiting the scope of the invention, which is defined by the appended claims.

What is claimed is:

1. A method for improving airway patency in a patient having an oral cavity, a hard palate, a soft palate, a tongue, and an airway, said method comprising:
    positioning an oral device in the oral cavity;
    applying a negative pressure from the device into posterior regions of the oral cavity while at least a first leg of said device is positioned along a side of the tongue, wherein the negative pressure is applied through the leg and causes the soft palate and tongue to form a seal whereby the patient's airway is fluidly isolated from the oral cavity anterior to the seal.

2. A method as in claim 1, further comprising delivering air to the oral cavity.

3. A method as in claim 2, wherein applying delivering air to the oral cavity comprises:
    applying a positive pressure from the device into posterior regions of the oral cavity along a side of the tongue.

4. A method as in claim 3, wherein the positive pressure is applied from a positive pressure lumen adjacent to the lumen applying the negative pressure the one side of the oral device.

5. A method as in claim 4, wherein the positive pressure is applied through a pair of positive pressure lumens, one on each side of the tongue.

6. A method as in claim 5, wherein the positive pressure is applied through a pair of positive pressure lumens which are adjacent to a pair of negative pressure lumens, one on each side of the tongue.

7. A method as in claim 1, wherein the negative pressure is applied from a lumen in the at least first leg on one side of the oral device.

8. A method as in claim 7, wherein the lumen is integral with or coupled to the oral device.

9. A method as in claim 7, wherein the vacuum is applied through ports on the lumen oriented toward the tongue.

10. A method as in claim 1, wherein the negative pressure is applied laterally from the device into posterior regions of the oral cavity along both sides of the tongue.

11. A method as in claim 10, wherein the negative pressure is applied through a pair of lumens, one on each side of the tongue.

12. A method as in claim 1, further comprising sealing the patient's lips to inhibit air entering the oral cavity while the vacuum is being applied.

13. A method as in claim 12, wherein sealing the patient's lips comprises positioning a sealing structure between the patient's lips and the patient's teeth.

14. A method as in claim 1, wherein the negative pressure in a range from −5 cm $H_2O$ to −150 cm $H_2O$.

15. A method as in claim 1, further comprising repositioning the patient's jaw from an undeflected position to a deflected position, and maintaining the jaw in the deflected position while the vacuum is applied.

16. A method as in claim 1, further comprising collecting saliva aspirated from the oral cavity by the vacuum.

\* \* \* \* \*